United States Patent
West et al.

(10) Patent No.: US 7,186,797 B2
(45) Date of Patent: Mar. 6, 2007

(54) POLYPEPTIDE CONJUGATES WITH EXTENDED CIRCULATING HALF-LIVES

(75) Inventors: Theodore R. West, Boston, MA (US); Thomas J McMurry, Winchester, MA (US); Stephane Dumas, Cambridge, MA (US); Andrew Kolodziej, Winchester, MA (US)

(73) Assignee: Epix Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 10/487,025

(22) PCT Filed: Aug. 9, 2002

(86) PCT No.: PCT/US02/25323
§ 371 (c)(1),
(2), (4) Date: Jul. 15, 2004

(87) PCT Pub. No.: WO03/013573
PCT Pub. Date: Feb. 20, 2003

(65) Prior Publication Data
US 2004/0254119 A1   Dec. 16, 2004

Related U.S. Application Data

(60) Provisional application No. 60/311,557, filed on Aug. 10, 2001.

(51) Int. Cl.
*C07K 1/113* (2006.01)
*C07K 2/00* (2006.01)
*C07K 14/435* (2006.01)

(52) U.S. Cl. .............. 530/303; 435/188; 514/7; 530/345; 530/351; 530/352; 530/409; 530/410; 544/214; 544/232

(58) Field of Classification Search ............. None
See application file for complete search history.

(56) References Cited

U.S. PATENT DOCUMENTS

| 5,233,023 | A | * | 8/1993 | Balkovec et al. ........... 530/317 |
| 5,677,450 | A | | 10/1997 | Suzuki et al. ............... 544/194 |
| 5,863,905 | A | | 1/1999 | Suhadolnik et al. ......... 514/44 |
| 5,962,437 | A | | 10/1999 | Kucera et al. ............... 514/77 |

FOREIGN PATENT DOCUMENTS

JP    63-275661 A   * 11/1988

OTHER PUBLICATIONS

Zobel et al., "Phosphate Ester Serum Albumin Affinity Tags Greatly Improve Peptide Half-Life In Vivo," *Bioorganic & Medicinal Chemistry Letters*, 2003, 13:1513-1515.
US 5,739,275, 04/1998, Pang et al. (withdrawn)*

* cited by examiner

Primary Examiner—Jeffrey Edwin Russel
(74) *Attorney, Agent, or Firm*—Fish & Richardson P.C.

(57) ABSTRACT

The present invention relates to compounds and methods for synthesizing compounds wherein the compounds exhibit extended circulating half-life in the blood. The increase in circulating half-life is achieved by conjugating polypeptides to binding groups that exhibit high affinity for human serum albumin.

44 Claims, 1 Drawing Sheet

POLYPEPTIDE CONJUGATES WITH EXTENDED CIRCULATING HALF-LIVES

CROSS-REFERENCE TO RELATED APPLICATIONS

This application is a National Stage application under 35 U.S.C. 371 and claims the benefit of International Application No. PCT/US02/25323 having an International Filing Date of Aug. 9, 2002, which claims the benefit of priority of U.S. Provisional Application Ser. No. 60/311,557 having a filing date of Aug. 10, 2001, both of which are incorporated herein in their entirety.

TECHNICAL FIELD

The present invention provides compounds that can be conjugated to a polypeptide to extend the circulating half-life of the polypeptide in the blood. More particularly, the invention provides compounds that exhibit high affinity for human serum albumin and polypeptides conjugated to such compounds.

BACKGROUND

Recombinant DNA techniques have permitted the commercial production of medically useful quantities of therapeutic polypeptides. The short half-life of many therapeutic polypeptides, however, has historically posed a challenge to the effective administration of these compounds. There are several commercially important polypeptide-based drugs currently in use which would benefit from increased half-life: Erythropoietin ($t_{1/2}$=180, min), insulin ($t_{1/2}$=5 min), interferon α-2b ($t_{1/2}$=120 min), interferon β ($t_{1/2}$=60 min), interferon γ ($t_{1/2}$=30 min), granulocyte colony stimulating factor ($t_{1/2}$=120 min), human growth hormone ($t_{1/2}$=30 min), granulocyte macrophage colony stimulating factor ($t_{1/2}$=120 min), relaxin ($t_{1/2}$=30 min), urokinase ($t_{1/2}$=50 min), streptokinase ($t_{1/2}$=80 min), tissue plasminogen activator ($t_{1/2}$=55 min), and tumor necrosis factor ($t_{1/2}$=18 min). Extending the half-life of therapeutic polypeptides can improve current therapies by allowing dosing amounts and frequency of dosing to be reduced.

SUMMARY

The invention is based on compounds that can be used to increase the half-life of a polypeptide in vivo. Such compounds can be used to modulate the pharmacokinetics and pharmacodynamics of therapeutic polypeptides by extending the half-life of the therapeutic polypeptides (e.g., insulin) by binding to serum albumin.

In one aspect, the invention features a compound having the formula:

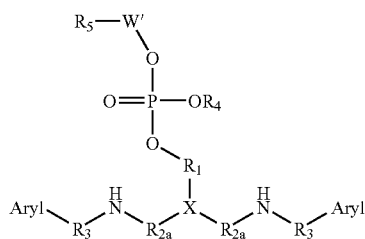

wherein $R_1$, $R_{2a}$ and $R_{2b}$, and $R_3$ independently comprise a linear chain of 0 to 12 atoms; $R_4$ is H, alkyl, or a negative charge and the salts thereof; X is one atom or 5 or more atoms, wherein the 5 or more atoms form a cyclic or a heterocyclic ring structure; and W' is a linker comprising at least one reactive moiety $R_5$. $R_1$ can be $(CH_2)_n$, where n is an integer from 0 to 12. $R_{2a}$ and $R_{2b}$ can be independently $(CH_2)_m$, $C(O)NH-(CH_2)_x$, $CH_2-NH-(CH_2)_y$, $(CH_2)_z-C(O)$, or not present, where m, x, and z are integers from 0 to 12 and y is an integer from 1 to 12. $R_3$ can be independently $C(O)-(CH_2)_p$, where p is an integer of 0 to 12, $C(O)CH(CH_3)$, $C(O)C(CH_3)_2$, or is not present. $R_5$ can be halogen, 1° amine, 2° amine, 3° amine, hydroxyl, thiol, carboxylic acid, sulfonic acid, or activated ester. X can be N, CH, P, or triazine.

The invention also features a compound having the formula,

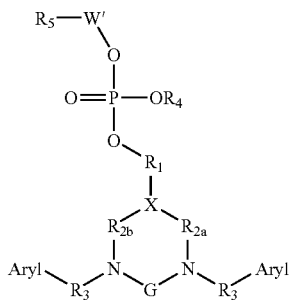

wherein $R_1$, $R_{2a}$ and $R_{2b}$, and $R_3$ independently comprise a linear chain of 0 to 12 atoms; $R_4$ is H, alkyl, or a negative charge and the salts thereof; X is one atom or 5 or more atoms, wherein the 5 or more atoms form a cyclic or a heterocyclic ring structure; W' is a linker comprising at least one reactive moiety $R_5$; and G is a chain of 0 to 9 atoms. $R_1$ can be $(CH_2)_n$, where n is an integer from 0 to 12. $R_{2a}$ and $R_{2b}$ can be independently $(CH_2)_m$, $C(O)NH-(CH_2)_x$, $CH_2-NH-(CH_2)_y$, $(CH_2)_z-C(O)$, or not present, where m, x, and z are integers from 0 to 12 and y is an integer from 1 to 12. $R_3$ can be independently $C(O)-(CH_2)_p$, where p is an integer of 0 to 12, $C(O)CH(CH_3)$, $C(O)C(CH_3)_2$, or is not present. $R_5$ can be halogen, 1° amine, 2° amine, 3° amine, hydroxyl, thiol, carboxylic acid, sulfonic acid, or activated ester. X can be N, CH, P, or triazine. G can be $(CH_2)_q$, where q is an integer from 0 to 9, C(O), $SO_2$, or S(O). W' can be a linear or branched alkyl chain having one or more carbon atoms. One or more of the carbon atoms can be substituted independently with cycloalkane, a heteroatom, a substituted heteroatom, CO—O, CO—NH, CO—S, CO, $SO_2$, $SO_2$—NH, or $SO_2$—O. The substituted heteroatom can be selected from the group consisting of N-(alkyl), N-(aryl), N-(alkylaryl), phosphine, phosphate, thiophosphate, phosphodiester, and aminophosphate. The aryl moieties can be independently

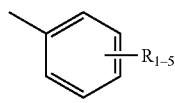

wherein R is selected from the group consisting of H, $OCH_3$, halogen, CN, $NO_2$, $CF_3$, $OCF_3$, OH, $O(C_1-C_4)$alkyl, SH, $S(C_1-C_4)$alkyl, $SO(C_1-C_4)$alkyl, $SO_2(C_1-C_4)$alkyl, $SO_3H$, $SO_2NH_2$, $SO_2NH(C_1-C_4)$alkyl, $NH_2$, $NH(C_1-C_4)$ alkyl, $N((C_1-C_4)alkyl)_2$, $CO_2H$, $(C_1-C_6)$alkyl, and $(C_3-C_8)$ cycloalkyl. Such compounds can be conjugated to a therapeutic polypeptide to increase the half life of the therapeutic polypeptide.

In another aspect, the invention features a conjugated polypeptide having the general Formula I

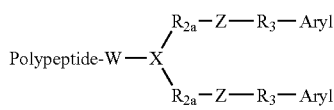
(I)

wherein $R_{2a}$, $R_{2b}$, and $R_3$ independently comprise a linear chain of 0 to 12 atoms; X is one atom or 5 or more atoms, wherein the 5 or more atoms form a cyclic or a heterocyclic ring structure; W is a linker; and Z is independently NH, O, S, S(O), $CH_2$, NH—CO, $SO_2$, CH—R, $C(R)_2$, CC, CH=CH, CH=N, wherein R is alkyl or aryl, wherein the conjugated polypeptide specifically binds to albumin. $R_{2a}$ and $R_{2b}$ can be independently $(CH_2)_m$, $C(O)NH-(CH_2)_x$, $CH_2-NH-(CH_2)_y$, $(CH_2)_z-C(O)$, or not present, where m, x, and z are integers from 0 to 12 and y is an integer from 1 to 12. $R_3$ can be independently $C(O)-(CH_2)_p$, where p is an integer of 0 to 12, $C(O)CH(CH_3)$, $C(O)C(CH_3)_2$, or is not present. X can be N, CH, P, or triazine.

In yet another aspect, the invention features a conjugated polypeptide having the general Formula II,

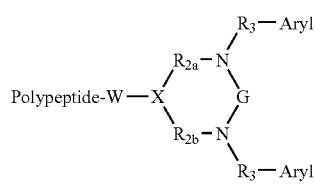
(II)

wherein $R_{2a}$, $R_{2b}$, and $R_3$ independently comprise a linear chain of 0 to 12 atoms; X is one atom or 5 or more atoms, wherein the 5 or more atoms form a cyclic or a heterocyclic ring structure; W is a linker; and G is a chain of 0 to 9 atoms, wherein the conjugated polypeptide specifically binds to albumin. $R_{2a}$, $R_{2b}$, $R_3$ and X are as discussed above. G can be $(CH_2)_q$, where q is an integer from 0 to 9, C(O), $SO_2$, or S(O).

The polypeptide can be selected from the group consisting of erythropoietin, insulin, interferon α-2b, inferferon β, interferon γ, granulocyte colony stimulating factor, human growth hormone, granulocyte macrophage colony stimulating factor, relaxin, urokinase, streptokinase, tissue plasminogen activator, and tumor necrosis factor. The conjugated polypeptides can specifically binds to site II of albumin. The conjugate also can exhibit a serum half-life that is greater than that of the corresponding unconjugated polypeptide.

W can be a structural element having the formula,

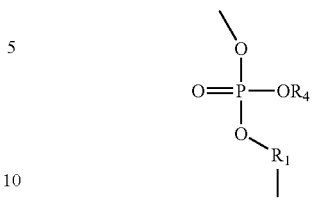

wherein $R_1$ is $(CH_2)_n$, where n is an integer from 0 to 12; and $R_4$ is H, alkyl, or a negative charge and the salts thereof.

W can include a structural element having the formula,

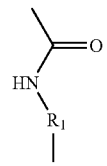

wherein $R_1$ is $(CH_2)_n$, where n is an integer from 0 to 12.

W also can be a linear or branched alkyl chain having one or more carbon atoms. One or more of the carbon atoms can be substituted independently with cycloalkane, a heteroatom, a substituted heteroatom, CO—O, CO—NH, CO—S, CO, $SO_2$, $SO_2$—NH, or $SO_2$—O. The substituted heteroatom is selected from the group consisting of N(Alkyl), N(Aryl), and N(Alkyl-Aryl), phosphine, phosphate, thiophosphate, phosphodiester, and aminophosphate. The aryl moieties are as discussed above.

In another aspect, the invention features a conjugated polypeptide having the general Formula III,

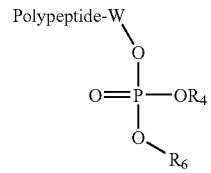

wherein, $R_4$ is H, alkyl, or a negative charge and the salts thereof; $R_6$ comprises one or more carbon atoms; and W is a linker, wherein the conjugated polypeptide binds albumin.

In another aspect, the invention features a compound having the formula

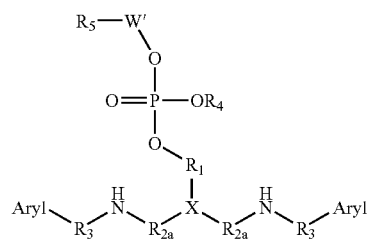

wherein $R_1$ is $(CH_2)_n$, where n is an integer from 0 to 12; $R_{2a}$ and $R_{2b}$ are independently $(CH_2)_m$, $C(O)NH-(CH_2)_x$, $CH_2$—NH—$(CH_2)_y$, $(CH_2)_z$—C(O), or not present; where m, x, and z are integers from 0 to 12 and y is an integer from 1 to 12; $R_3$ is independently C(O)—$(CH_2)_p$, where p is an integer of 0 to 12, C(O)CH(CH$_3$), C(O)C(CH$_3$)$_2$, or is not present; $R_4$ is H, alkyl, or a negative charge and salts therof; X is N, CH, P, or triazine; W' is a linker having at least one reactive moiety $R_5$, wherein $R_5$ is selected from the group consisting of halogen, 1° amine, 2° amine, 3° amine, hydroxyl, thiol, carboxylic acid, sulfonic acid, and activated ester. In some embodiments, n is 1; $R_{2a}$ is $CH_2$—NH═ $(CH_2)_2$, $R_{2b}$ is not present, $R_4$ is H; and X is CH. In other embodiments, n is 1; $R_{2a}$ is C(O)—NH—$(CH_2)_2$, $R_{2b}$ is not present, $R_4$ is H; and X is CH or n is 1; $R_{2a}$ is $CH_2$, $R_{2b}$ is not present, $R_4$ is H; and X is CH.

In yet another aspect, the invention features a compound having the formula,

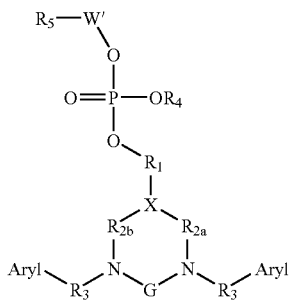

wherein $R_1$ is $(CH_2)_n$, where n is an integer from 0 to 12; $R_{2a}$ and $R_{2b}$ are independently $(CH_2)_m$, C(O)NH—$(CH_2)_x$, $CH_2$—NH—$(CH_2)_y$, $(CH_2)_z$—C(O), or not present; where m, x, and z are integers from 0 to 12 and y is an integer from 1 to 12; $R_3$ is independently C(O)—$(CH_2)_p$, where p is an integer of 0 to 12, C(O)CH(CH$_3$), C(O)C(CH$_3$)$_2$, or is not present; $R_4$ is H, alkyl, or a negative charge and salts therof; X is N, CH, P, or triazine; W' is a linker having at least one reactive moiety $R_5$, wherein $R_5$ is selected from the group consisting of halogen, 1° amine, 2° amine, 3° amine, hydroxyl, thiol, carboxylic acid, sulfonic acid, and activated ester; and G is $(CH_2)_q$, where q is an integer from 0 to 9, C(O), SO$_2$, or S(O).

In some embodiments, one or both aryl groups are replaced with a non-aromatic moiety having 1–10 carbon atoms. The non-aromatic moiety can include a linear, branched, or cyclic alkyl, alkenyl, or alkynyl moiety. The cyclic moiety can be one or more heteroatoms (e.g., N, O, and S).

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Definitions

Figure 1:
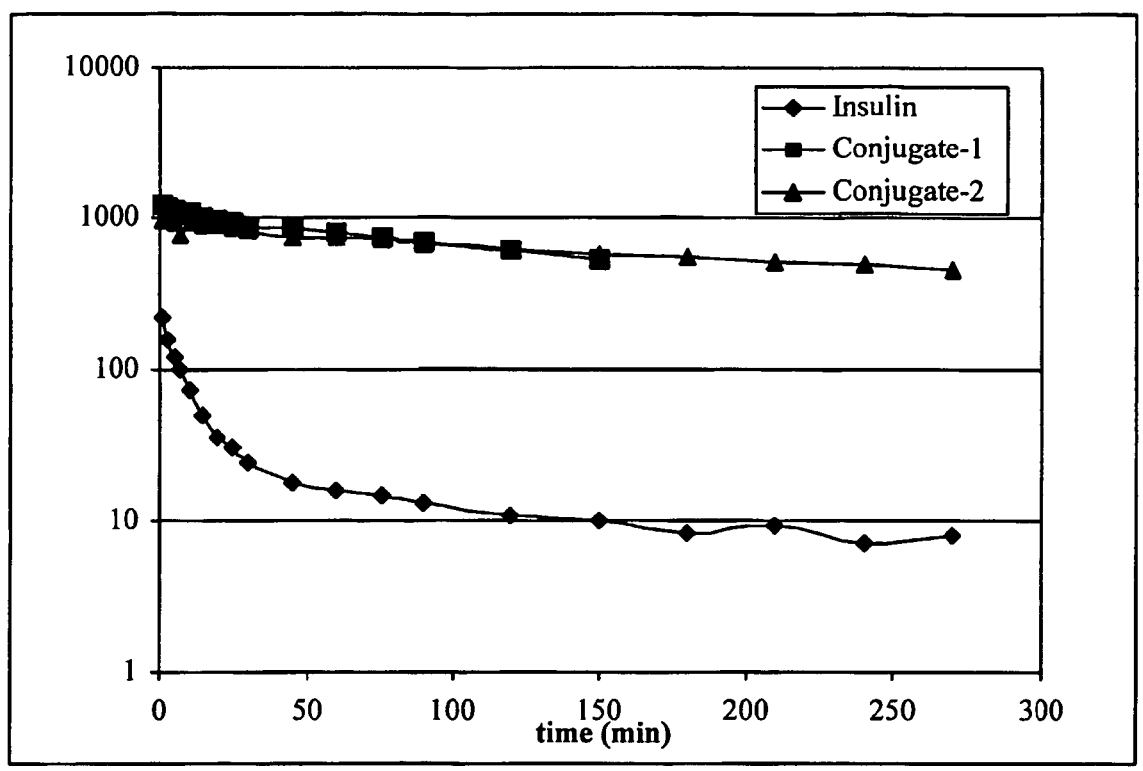
FIG. 1 is a plot showing rabbit plasma pharmacokinetic data for insulin (diamond), conjugate-1 (squares) and conjugate-2 (triangles). Concentrations of insulin or insulin conjugates were determined following HPLC speciation of the total $^{125}$I.

Commonly used chemical abbreviations that are not explicitly defined in this disclosure may be found in The American Chemical Society Style Guide, Second Edition; American Chemical Society, Washington, D.C. (1997), "2001 Guidelines for Authors" *J. Org. Chem.* 66(1), 24A (2001), "A Short Guide to Abbreviations and Their Use in Polypeptide Science" *J. Polypeptide. Sci.* 5, 465–471 (1999).

The term "polypeptide" refers to a chain of at least two amino acids, regardless of post-translational modifications. Polypeptides can be naturally occurring, chemically synthesized, or recombinantly produced polymers of amino acids. Polypeptides that have two to 50 amino acids typically are classified as peptides.

The term "enzyme" means a polypeptide with catalytic activity.

The term "insulin" as used herein refers to the naturally occurring hypoglycemic polypeptide found in mammals, including humans, rat, guinea pig, and rabbits, as well as similar hypoglycemic polypeptides disclosed in U.S. Pat. Nos. 4,652,525, 4,431,740, 5,268,453, 5,506,202, 5,514, 646, and 5,700,662.

The term "substituted" includes substituents which can be placed on the moiety and which allow the molecule to perform its intended function.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$–$C_6$ for straight chain, $C_3$–$C_6$ for branched chain), and more preferably 4 or fewer. Likewise, preferred cycloalkyls have from 3–8 carbon atoms in their ring structure, and more preferably have 5 or 6 carbons in the ring structure. The term $C_1$–$C_6$ includes alkyl groups containing 1 to 6 carbon atoms.

The term "alkenyl" includes unsaturated aliphatic groups analogous in length and possible substitution to the alkyls described above, but that contain at least one double bond and must contain at least two carbon atoms. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$–$C_6$ for straight chain, $C_3$–$C_6$ for branched chain). Likewise, cycloalkenyl groups may have from 3–8 carbon atoms in their ring structure, and more preferably have 5 or 6 carbons in the ring structure. The term $C_2$–$C_6$ includes alkenyl groups containing 2 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "arylalkyl" moiety is an alkyl substituted with an aryl (e.g., phenylmethyl (benzyl)). The term "n-alkyl" means a straight chain (i.e. unbranched) unsubstituted alkyl group.

In general, the term "aryl" includes groups, including 5- and 6-membered single-ring aromatic groups that may include from zero to four heteroatoms, for example, benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heterocycles," "heteroaryls," or "heteroaromatics." An aryl group may be substituted at one or more ring positions with substituents.

Polypeptide Conjugates

In general, the invention provides polypeptide conjugates that have extended half lives in vivo. Polypeptides typically are conjugated to binding moieties that have affinity for serum albumin (e.g., human serum albumin (HSA)). HSA is a 585 amino acid polypeptide that functions as a carrier of endogenous and exogenous ligands. HSA can bind molecules having a lipophilic portion and either negative charges at physiological pH or partial negatively charged oxygens, sulphurs, or fluorines. In general, binding affinity to HSA increases with the hydrophobicity of the binding moiety. A wide range of hydrophobic or amphiphilic binding moieties can be used, including, for example, aliphatic or aryl groups with 1 to 60 carbons containing any number of nitrogen, oxygen, sulfur, halogen, alkyl, amide, ester, and sulfonamide substituents. Mixed aliphatic-aryl or aryl groups are particularly useful. Alternatively, the binding group may be a peptide containing hydrophobic amino acid residues and/or substituents, with or without hydrophobic or hydrophilic termination groups. Binding groups that do not displace thyroxine from albumin are particularly useful, as displacement of thyroxine may lead to untoward effects. In addition, binding groups that do not displace warfarin or digoxin from albumin also can be desirable.

Binding groups that have an affinity for serum albumin of greater than 50% (e.g., greater than 60, 70, 80, 90, or 95%) bound under physiological conditions are suitable. In general, a compound that binds to albumin to a higher degree will have a longer half-life in the blood. A range of albumin binding properties can be used, however, to tailor the half-life of a conjugated polypeptide to a suitable level. For example, binding should be strong enough to extend the half life, but not so strong that there is no free fraction of the conjugate available to exert a beneficial physiological effect. If some degree of extravasation is desired, an albumin binding group of intermediate affinity may be chosen.

Binding groups that have a strong affinity for a specific site on albumin are particularly useful as such information can be used to predict drug displacement reactions that may occur in vivo. HSA contains three homologous domains, with each domain composed of two subdomains that share structural motifs. While HSA contains many binding sites for endogenous and exogenous molecules, sites I and II are the principal regions of ligand binding. See for example, Sudlow, G. et al. *Molecular Pharmacology* 1975, 11, 824–832; and Sudlow, G. et al. *Molecular Pharmacology* 1976, 12, 1052–1061. Site I is a large site existing on subdomain IIA and is capable of binding a diverse range of molecules including warfarin and salicylate. Binding affinity to site I can be assessed using warfarin, dansyl-L-asparagine (DNSA), and n-butylp-aminobenzoate fluorescent probes. See, for example, Yamasaki, K. et al. *Biochimica et Biophysica Acta* 1996, 1295, 147–157. Site II is located on subdomain IIIA and binds molecules such as diazepam, ibuprofen, and naproxen. See, for example, Peters, T. J. *All About Albumin: Biochemistry, Genetics, and Medical Applications*; Academic Press: San Diego, 1996. Conjugated polypeptides of the invention can specifically bind to site II of albumin.

Methods for determining the albumin affinity of candidate binding groups and the albumin affinity of polypeptide conjugates are known in the art and include affinity chromatography, size exclusion chromatography, equilibrium dialysis, and fluorescent probe displacement. In cases where the solubility of the binding groups alone is limited, it may be desirable to assess the relative affinity by derivatizing the binding group with a solubilizing fragment (e.g., Gd-DTPA). For example, HSA binding can be assessed by equilibrium dialysis or ultrafiltration using 4.5% weight/volume HSA in a buffer (pH 7.4). In fluorescent probe displacement, a fluorescent probe that fluoresces when bound to HSA is used. Affinity is assessed by determining if the fluorescent probe is displaced from the binding site on HSA by the albumin binding moiety. A decrease in fluorescence indicates that the albumin binding moiety displaced the probe and the resulting data can be fit to obtain an inhibition equilibrium constant, $K_i$, which reflects the affinity of the binding group for a given probe's binding site.

Albumin binding moieties can be conjugated to any therapeutic polypeptide. For example, the polypeptide can be a bioactive peptide (e.g., 5 to 50 amino acids in length) or can be a longer polypeptide that may or may not have catalytic activity. Non-limiting examples of bioactive peptides include neurotransmitters such as conantokin G, dynorphin, endorphin, enkelphalin, or neurotensin; gastric activators such as bombesin, motilin, or gastrin; calcium regulators such as calcitonin; hormones such as vasoactive intestinal polypeptide, corticotropin, or secretin; hormone inhibitors such as somatostatin; hormone stimulators such as melanocyte stimulating hormone, luteinizing hormone releasing factor, or sermorelin; anti-diabetic agents such as glucagons or insulin ("Humulin," Eli Lilly); vasoconstrictors such as angiotensin II; vasodilators such as bradykinin, substance P, or kallidin; natriuretic agents such as atrial natriuretic polypeptide; and oxytocic agents such as oxytocin. Additional examples of polypeptides that can be used include human growth hormone ("Humantrope," Genentech); G-CSF ("Neupogen," Amgen); erythropoietin ("Epogen," Amgen); interferon α, β, or γ; factor VIII or other blood clotting factors such as protein C or factor VIIa; follicle stimulating hormone; a cytokine such as an interleukin (IL) (e.g., IL-1, -2, -3, -4, -5, -6, -7, -8, -9, -10, -11, or -12); hemoglobin; superoxide dismutase; soluble CD4 or CD4 receptor; soluble TNF receptor ("Enbrel," Immunex); platelet gpIIb/IIIa analogs and their receptors ("ReoPro," Johnson & Johnson); glucocerebrosidase ("Ceredase" or "Cerezyme," Genzyme); ACTH; somatotropin; parathyroid hormone, antidiuretic hormone; prolactin; or thrombolytics such as streptokinase, staphylokinase, urokinase, or tissue plasminogen activator ("Activase," Genentech).

Polypeptide conjugates that specifically bind to albumin can have general Formula I:

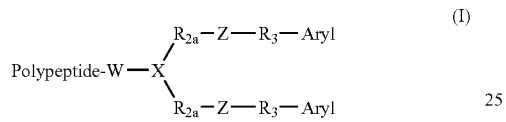

(I)

$R_{2a}$, $R_{2b}$, and $R_3$ independently can include a linear chain of 0 to 12 atoms. For example, $R_{2a}$ and $R_{2b}$ can be present or not. If present, $R_{2a}$ and $R_{2b}$ can be the same or different and can include, for example, $(CH_2)_m$, NH, $C(O)NH—(CH_2)_x$, $CH_2—NH—(CH_2)_y$, $(CH_2)_z—C(O)$, where m, x, and z are integers from 0 to 12 and y is an integer from 1 to 12.

$R_3$ can be, for example, $C(O)—(CH_2)_p$, where p is an integer of 0 to 12, $C(O)CH(CH_3)$, $C(O)C(CH_3)_2$. In some embodiments, $R_3$ is not present.

X can be one atom or 5 or more atoms, wherein the 5 or more atoms form a cyclic or a heterocyclic ring structure. For example, X can include any atom or group of atoms that provides a bifurcation point, such as, for example, N, CH, P, or triazine;

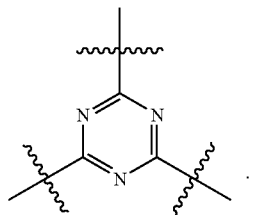

Z can be independently NH, O, S, S(O), $CH_2$, NH—CO, $SO_2$, CH—R, $C(R)_2$, CH=CH, CH=N, CC, wherein R is alkyl or aryl.

Any aryl moiety can be included in the conjugated polypeptide of the invention. Aryl moieties include those with the structural formula;

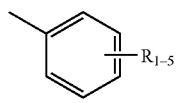

wherein the aryl moiety may be substituted with 1 to 5 R groups. R can be independently selected from H, $OCH_3$, halogen, CN, $NO_2$, $CF_3$, $OCF_3$, OH, $O(C_1–C_4)$Alkyl, SH, $S(C_1–C_4)$Alkyl, $SO(C_1–C_4)$Alkyl, $SO_2(C_1–C_4)$Alkyl, $SO_3H$, $SO_2NH_2$, $SO_2NH(C_1–C_4)$Alkyl, $NH_2$, $NH(C_1–C_4)$Alkyl, $N((C_1–C_4)$Alkyl$)_2$, $CO_2H$, $(C_1–C_6)$Alkyl, and $(C_3–C_8)$Cycloalkyl.

Exemplary aryl groups include those having the following structural formulae:

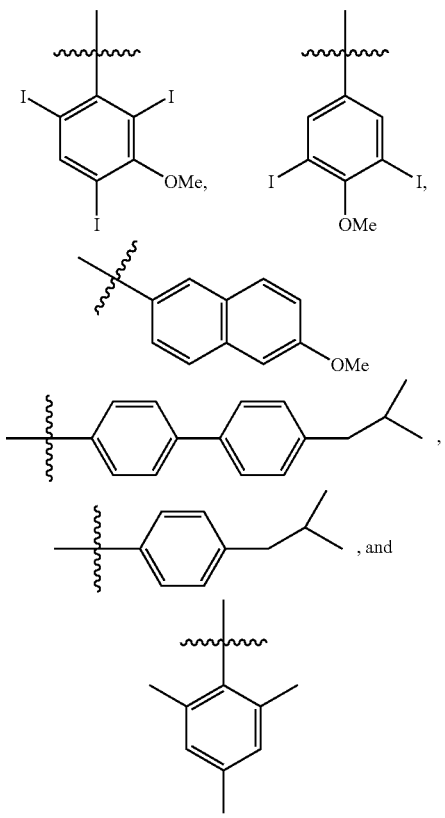

W is a linker that can be a linear or branched alkyl chain having one or more carbon atoms. One or more of the carbon atoms may be substituted independently with one or more of the following groups: a cycloalkane, a heteroatom, a substituted heteroatom, CO—O, CO—NH, CO—S, CO, $SO_2$, $SO_2$—NH, or $SO_2$—O. Exemplary substituted heteroatoms include, for example, N-(Alkyl), N-(Aryl), N-(Alkyl-Aryl), phosphine, phosphate, thiophosphate, aminophosphate, and phosphodiester.

An exemplary class of linkers (W) substituted with a phosphodiester moiety include those having the structural formula:

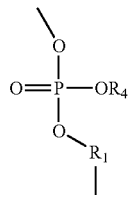

wherein $R_1$ is $(CH_2)_n$, where n is an integer from 0 to 12; and $R_4$ is H, alkyl, or a negative charge, and the salts thereof. Exemplary compounds having a phosphodiester moiety include those shown in Table 1 in the Examples.

To produce a conjugated polypeptide containing such a linker, a compound having the structural formula:

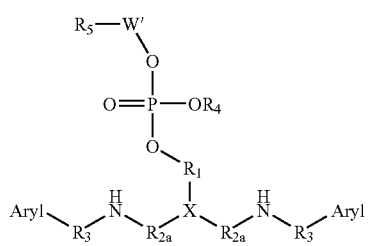

where $R_{2a}$, $R_{2b}$, $R_3$, $R_4$, and $R_5$ are as discussed above, can be used.

Linker W' includes at least one reactive moiety $R_5$. A "reactive moiety" is a chemical entity that can react with a polypeptide to form a covalent bond. Reagents for synthesizing polypeptide derivatives are well known in the art and include, without limitation, those approaches illustrated in "Techniques in Protein Modification," by Roger L. Lunblad (1994). Many types of reactions may be used for conjugation, which include acylation using active esters (U.S. Pat. No. 4,897,255), reductive amination, nucleophilic displacement reactions (e.g., bromoacetamide (U.S. Pat. No. 4,678,667)), urea formation, thiourea formation, and chemoselective ligation. Preferred reagents for modification of thiol residues on proteins include maleimides, haloacetamides, haloacetates, and dithiols, which form mixed disulfide adducts with the protein. Preferred reagents for modification of amino residues, such as the epsilon amino group of lysine, include active esters (e.g., anhydrides, pentafluorophenol, N-hydroxysuccinimide etc.), isothiocyanates, aldehydes (e.g., pyridoxal-5'-phosphate in a reductive amination scheme), haloacetamides, and haloacetates. Arginine residues may be modified with 2,3-butadione and borate.

Exemplary reactive moieties include H, halogen, 1° amine, 2° amine, hydroxyl, thiol, carboxylic acid, sulfonic acid, and activated ester. Activated esters are described in greater detail in M. Bodanszky, "Principles of Polypeptides Synthesis" 2nd ed.; Springer-Verlag, 1993, p. 276. Examples of a particularly preferred activated esters include NHS esters, carboxylate, acid chloride, acid anhydride, maleimide, and aldehyde.

Another class of linkers (W) substituted with an amide moiety can have the structural formula:

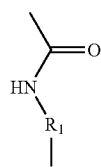

Conjugated polypeptides can be produced using such a linker to produce the following conjugate:

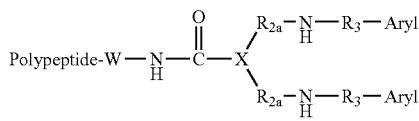

A second class of polypeptide conjugates that specifically binds to albumin have general structural Formula II:

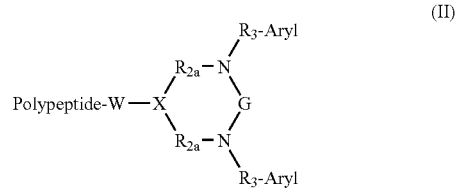

(II)

wherein $R_{2a}$, $R_{2b}$, $R_3$, W, and Aryl are as defined above. G is a chain of 0 to 9 atoms and can be any structural element that provides a ring size of between 5 and 12 atoms. For example, G can be $(CH_2)_q$, where q is an integer from 0 to 9, C(O), $SO_2$, or S(O).

To produce such a conjugated polypeptide, a compound having the structural formula:

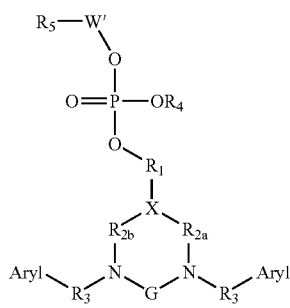

can be used, where the R groups are as defined above.

The stability of conjugates can be improved when either $R_{2a}$ or $R_{2b}$ is not present by limiting $R_1$ to $(CH_2)_n$, where n is an integer from 1 to 12.

A third class of conjugated polypeptides has the general Formula III,

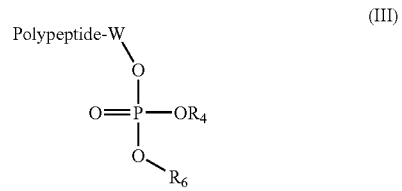

(III)

wherein W and $R_4$ are as described above. $R_6$ is a binding moiety that includes one or more carbon atoms. Albumin binding moieties are particularly useful. See, for example, the binding moieties described above and in Table I. It is noted that both W and W' in the above compounds and conjugates may contribute to albumin binding.

In one embodiment, the albumin binding moieties of the invention can be prepared, in general, by reacting a phosphoramidite protected compound having a reactive carboxylic acid moiety with a compound having a free hydroxyl moiety, a bifuircation point, and an aryl group to form a compound including a phosphodiester moiety, a terminal group, and a terminal carboxyl acid group. Phosphoramidites and compounds containing bifurcation points can be synthesized using standard synthetic methods and are well known to those skilled in the art. A second aryl moiety may be introduced using standard synthetic procedures, thus generating an albumin binding moiety having a bifurcation point, a phosphodiester, two aryl moieties, and a free carboxylic acid terminus. The free carboxylic acid terminus may be converted into an activated ester or other suitable moiety for conjugating to the amine terminus of a polypeptide. The following shows a general procedure for the preparation of such a compound:

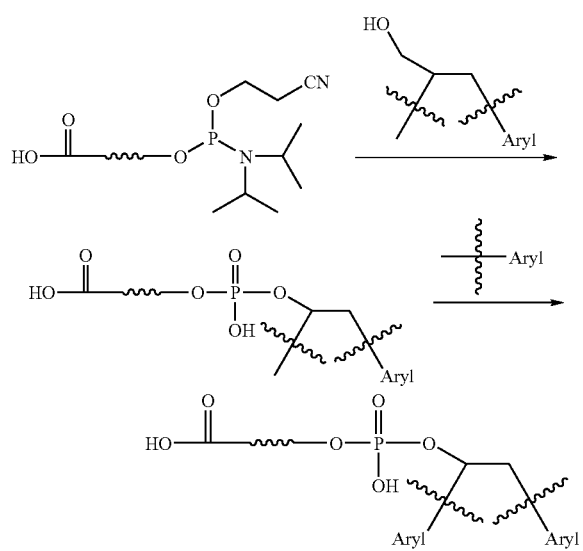

Pharmaceutical Compositions

Compositions of the invention, including albumin-binding moieties and polypeptide conjugates, can be formulated as a pharmaceutical composition in accordance with routine procedures. As used herein, the compounds of the invention can include pharmaceutically acceptable derivatives thereof. "Pharmaceutically acceptable" means that the compound or composition can be administered to an animal without unacceptable adverse effects. A "pharmaceutically acceptable derivative" means any pharmaceutically acceptable salt, ester, salt of an ester, or other derivative of a compound of this invention that, upon administration to a recipient, is capable of providing (directly or indirectly) a compound of this invention or an active metabolite or residue thereof. Other derivatives are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) thereby increasing the exposure relative to the parent species. Pharmaceutically acceptable salts of the compounds of this invention include counter ions derived from pharmaceutically acceptable inorganic and organic acids and bases known in the art.

Pharmaceutical compositions of the invention can be administered by any route, including both oral and parenteral administration. Parenteral administration includes, but is not limited to, subcutaneous, intravenous, intraarterial, interstitial, intrathecal, and intracavity administration. When administration is intravenous, pharmaceutical compositions may be given as a bolus, as two or more doses separated in time, or as a constant or non-linear flow infusion. Thus, compositions of the invention can be formulated for any route of administration.

Typically, compositions for intravenous administration are solutions in sterile isotonic aqueous buffer. Where necessary, the composition may also include a solubilizing agent, a stabilizing agent, and a local anesthetic such as lidocaine to ease pain at the site of the injection. Generally, the ingredients will be supplied either separately, e.g. in a kit, or mixed together in a unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection," saline, or other suitable intravenous fluids. Where the composition is to be administered by injection, an ampule of sterile water for injection or saline may be provided so that the ingredients may be mixed prior to administration. Pharmaceutical compositions of this invention comprise the compounds of the present invention and pharmaceutically acceptable salts thereof, with any pharmaceutically acceptable ingredient, excipient, carrier, adjuvant or vehicle.

Pharmaceutical compositions of this invention can be administered to mammals including humans in a manner similar to other diagnostic or therapeutic agents. The dosage to be administered, and the mode of administration will depend on a variety of factors including age, weight, sex, condition of the patient and genetic factors, and will ultimately be decided by medical personnel subsequent to experimental determinations of varying dosage followed by imaging as described herein. In general, dosage required for diagnostic sensitivity or therapeutic efficacy will range from about 0.001 to 50,000 µg/kg, preferably between 0.01 to 25.0 µg/kg of host body mass. The optimal dose will be determined empirically following the disclosure herein.

EXAMPLES

The following Examples are provided to illustrate the present invention and should not be construed as limiting thereof.

Example 1

Synthesis and Characterization of Albumin Binding Reagents

Step 1: (R)-2-Hydroxymethyl-N-trityl-(S)-4-isobutyl-N'-methylphenylacetyl ethylenediamine mono amide

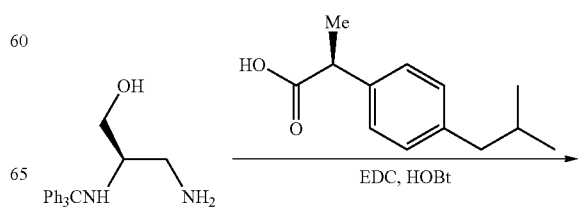

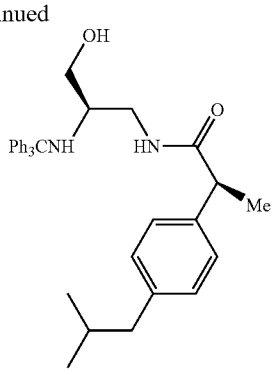

In a 100 mL round-bottom flask (R)-hydroxymethyl N-trityl ethylene diamine (1.33 g), (S)-Ibuprofen [(S)-(+)-4-Isobutyl-α-methylphenylacetic acid] (0.83 g) and HOBt.1H$_2$O (0.68 g) were dissolved in 10 mL anhydrous methylene chloride. EDC (0.96 g, 5 mmol, 1.25 eq) was added at 5°. The mixture was stirred between 5° C. and room temperature for 24 h. Methylene chloride was evaporated by rotary evaporation, and the residue was dissolved in ethyl acetate. The ethyl acetate layer was washed twice with H$_2$O and dried over MgSO$_4$. Evaporation of solvent gave 2.16 g of the crude desired amide as a white foaming solid. The amide was purified by flash chromatography on silica gel (hexane/ethyl acetate). Yield 1.62 g (78%). MS: 543.55 (M+Na).

Step 2: (R)-2-Hydroxymethyl-N-(S)-4-isobutyl-α-methylphenylacetyl-ethylenediamine amide

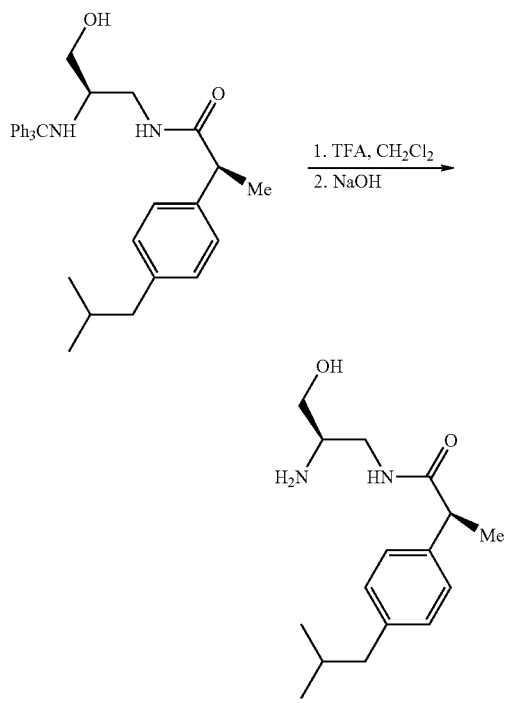

In a 10 mL round-bottom flask tritylated amine was dissolved in 2.5 mL anhydrous methylene chloride. TFA (2.5 mL) was added drop-wise. After 5 minutes the solvents were evaporated by rotary evaporation and the residue solidified on standing on the vacuum line. The residue was triturated with 1N HCl and was extracted with ethyl acetate. The organic layer was dried over Na$_2$SO$_4$. Evaporation of solvent gave 0.937 g of crude desired amide as a trifluoroacetate salt. The free amine was liberated with 8N NaOH (pH=9). The aqueous layer was extracted with ethyl acetate twice. The organic layers were combined and dried over MgSO$_4$. Evaporation of solvent gave the desired amide as a white solid. Yield 0.211 g (62%). MS: 301.35 (M+Na).

Step 3: (R)-2-Hydroxymethyl-N-(S)-4-isobutyl-α-methylphenylacetyl-N'-(S)-benzyloxycarbonyl t-butyl aspartyl ethylenediamine diamide

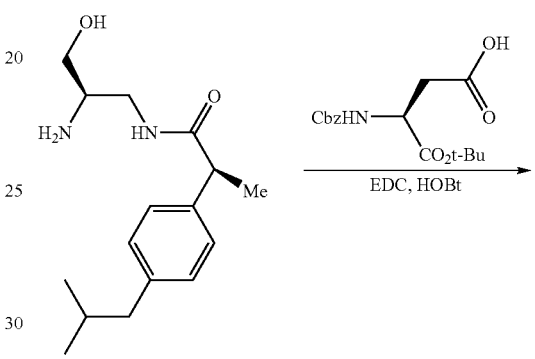

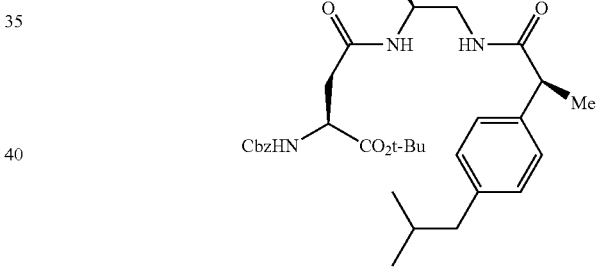

(S)-Benzyloxycarbonyl-t-butyl-aspartate was obtained by treatment of the corresponding dicyclohexylamine salt with 0.5N KHSO$_4$ and extraction with ethyl acetate. The free acid, the amine and the HOBt mono hydrate were dissolved in 20 mL methylene chloride at 0° C. EDC (0.395 g) was added. The reaction was stirred for 16 h at RT. Methylene chloride was evaporated by rotary evaporation and the residue was dissolved in ethyl acetate. The ethyl acetate layer was washed with H$_2$O (2×100 mL) and with brine (100 mL) and dried over MgSO$_4$. Evaporation of solvent gave the crude desired product, which was purified by flash chromatography on silica gel (CH$_2$Cl$_2$/MeOH). Yield 0.613 g (63%). MS: 584.65 (M+1).

Step 4: mono-Benzyl glutaric acid

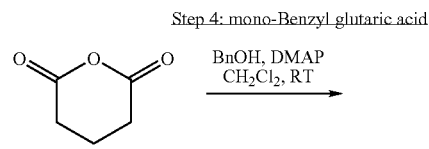

-continued

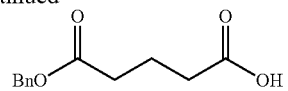

Glutaric anhydride (3.423 g) and benzyl alcohol (3.10 mL) were dissolved in methylene chloride. DMAP (0.183 g) was added and the reaction mixture was stirred at RT for 22 h. The solvent was evaporated and the residue was dissolved in ethyl acetate. The organic layer was extracted with 40 ml 1N NaOH and with 40 mL $H_2O$. The aqueous layers were combined and extracted with ethyl acetate. The aqueous layer was acidified to pH 3 with 6N HCl solution and was extracted with ethyl acetate (3×30 ml). The organic layers were combined and dried over $MgSO_4$. The solvent was removed by rotary evaporation to give 2.79 g of a mixture of a 6:5 ratio of desired mono-ester and glutaric acid. The crude mono ester was used without any further purification in the next step.

Step 5:
Cyanoethyl-N,N-diisopropyl(benzyl-5-hydroxy pentanoate) phosphoramidite

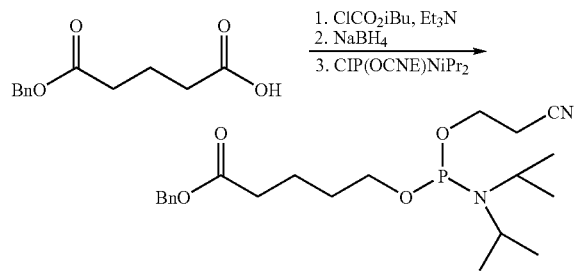

The 6:5 mixture of mono-benzyl glutarate and glutaric acid (2.79 g, 1.88 g of mono ester) was dissolved in 20 mL anhydrous THF. Triethylamine (1.53 mL) was added at 0° C. iso-Butyl chloroformate (1.25 mL) was added drop-wise and the resulting suspension was stirred for 15 minutes at 0° C. The triethylamine hydrochloride salt was filtered and the filtrate was added drop-wise to a solution of $NaBH_4$ (0.963 g) in $H_2O$ in 15 minutes at 0° C. The reaction mixture was stirred for 20 minutes and the THF was removed by rotary evaporation. The residue was partitioned between ethyl acetate and 1N HCl. The aqueous layer was extracted with 3×30 mL ethyl acetate. The organic layers were combined and dried over $MgSO_4$. Evaporation of solvent gave 2.89 g of a mixture of starting mono-benzyl glutarate and the desired product which were separated by flash chromatography on silica gel (hexanes/ethyl acetate). First fraction: mono-benzyl glutarate (0.745 g, 40%), second fraction: benzyl 5-Hydroxy-pentanoate (0.839 g, 48%).

Benzyl 5-Hydroxy-pentanoate (0.657 g) was dissolved in 20 mL anhydrous methylene chloride and the solution was cooled to 0° C. Diisopropylethylamine (0.82 mL) followed by 2-cyanoethyl diisopropylchlorophosphoramidite (0.74 mL) were added at 0° C. The reaction mixture was stirred for 2 h between 0° C. and RT. The reaction mixture was washed with a cold and saturated $NaHCO_3$ solution and the organic layer was dried over $Na_2SO_4$.

Evaporation of the solvent gave 1.481 g of the crude desired phosphoramidite which was purified by flash chromatography on silica gel (hexanes/ethyl acetate/triethylamine). Yield 0.839 g (65%).

Step 6: Methyl 3-methoxy-2,4,6-triiodobenzoate

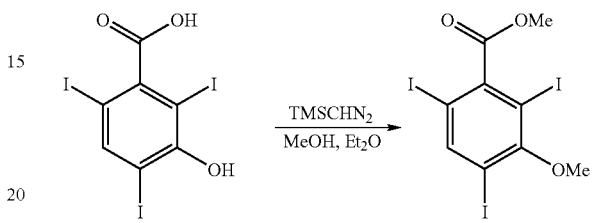

In a 3-neck 250 mL round-bottom flask fitted with a thermometer and a condenser, 3-methoxy-2,4,6-triiodobenzoic acid (10.38 g) was dissolved in a 2:1 mixture of $Et_2O$ and methanol at 0° C. A 2.0 M hexanes solution of $TMSCHN_2$ was added dropwise until yellow color persisted and $N_2$ bubbling stopped. The reaction mixture was stirred for 30 minutes and quenched with glacial acetic acid. Solvents and excess AcOH were removed in vacuo for 18 h to give the desired ester as a white solid which was used in the next step without any further purification. Yield 11.07 g (~100% crude).

Step 7: 3-methoxy-2,4,6-triiodobenzoic acid

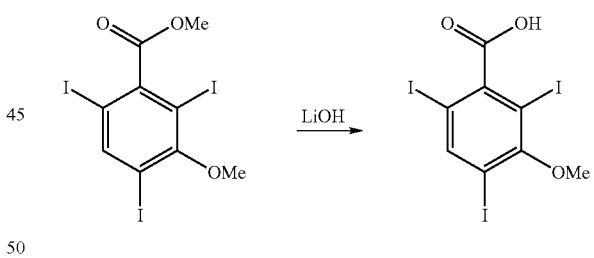

In a 250 mL round-bottom flask equipped with a condenser, methyl 3-methoxy-2,4,6-triiodobenzoate (11.07 g) was dissolved in a 3:1 mixture of dioxane/ MeOH (88 mL). Lithium hydroxide (1.71 g) dissolved in 22 mL $H_2O$ was added and the reaction mixture was stirred for 72 h at 60° C. Dioxane and methanol were evaporated and the residue was diluted with 100 mL $H_2O$. The aqueous solution was filtered and the filtrate was extracted with $Et_2O$ (2×100 mL). The ether layers were combined and dried over $MgSO_4$. Evaporation of solvent gave 7.64 g of un-reacted starting material (69%). The aqueous layer was acidified to pH 2 with 2N HCl and was extracted with ethyl acetate (3×100 mL). The combined organic layers were dried over $MgSO_4$. Evaporation of solvent gave the desired acid. Yield 3.14 g (29%).

Step 8: 3-methoxy-2,4,6-triiodobenzoyl chloride

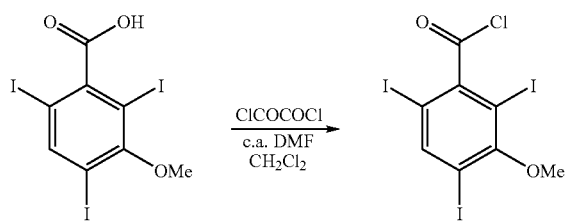

In a 25 mL round-bottom flask equipped with a condenser, methyl 3-methoxy-2,4,6-triiodobenzoic acid (0.250 g) was suspended in 3 mL anhydrous methylene chloride. Oxalyl chloride (0.58 mL) and one drop of DMF was added. The reaction mixture was stirred for 4 h at RT. The solvent and excess oxalyl chloride were removed by rotary evaporation. The desired acyl chloride was dried under vacuum to give a pale yellow solid which was used in the next step without any further purification. Yield 0.272 g (crude ~100%)

Step 9: Benzyl 5-oxy-pentanoate-phosphono-(R)-2-oxymethyl-N-(S)-4-isobutyl-α-methylphenylacetyl-N'-(S)-N-benzyloxycarbonyl t-butyl aspartyl ethylenediamine diamide

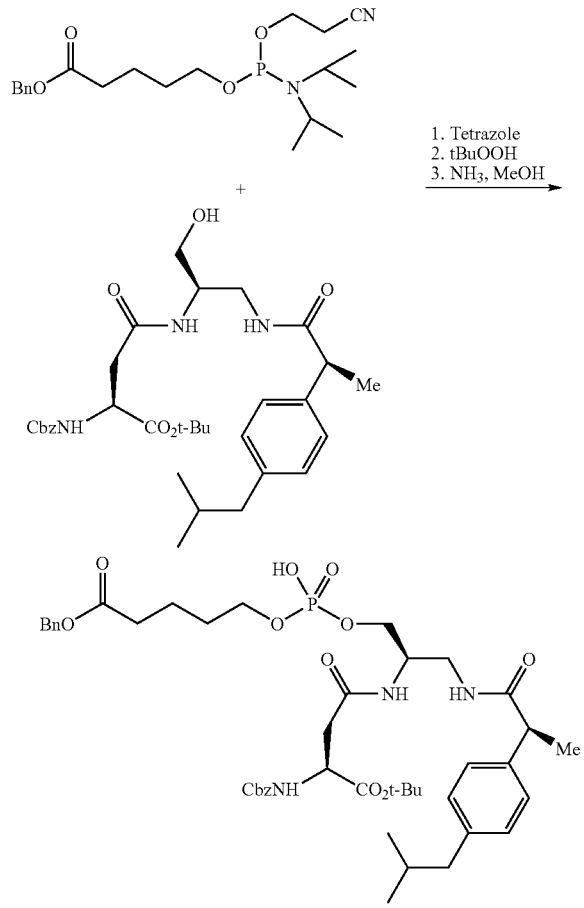

(R)-2-Hydroxymethyl-N-(S)-(+)-4-Isobutyl-α-methylphenylacetyl-N'-(S)-benzyloxycarbonyl t-butyl aspartyl-ethylenediamine diamide was suspended and cyanoethyl-N,N-diisopropyl(benzyl 5-hydroxy pentanoate) phosphoramidite was dissolved in 5 mL anhydrous acetonitrile and 2 g of molecular sieves 4 Å (2 g) was added. Tetrazole (0.088 g) was added at 0° C. After 1 h, 90% tBuOOH (0.175 mL, 1.58 mmol., 1.5 eq.) was added and the reaction was stirred for 45 minutes. The sieves were filtered and the filtrate was evaporated to dryness. The residue containing the crude phosphotriester was dissolved in ethyl acetate and was washed with $H_2O$, $Na_2S_2O_3$ and brine. The organic layer dried over $MgSO_4$. Evaporation of solvent gave 0.940 g of crude phosphodiester which was treated with 2M $NH_3$ in MeOH (10 mL). The mixture was stirred for 1 h at 0° C. and for 5 h at RT. The reaction was monitored by LC-MS. Evaporation of solvent gave 0.796 g of desired crude phophodiester ammonium salt which was purified by flash chromatography on silica gel ($CH_2Cl_2$/i-PrOH/$Et_3N$). Yield 0.613 g ($Et_3NH^+$ salt, 61%). MS: 853.95 (M+1).

Step 10: Oxy-pentanoic acid-phosphono-(R)-2-oxymethyl-N-(S)-4-isobutyl-α-methylphenylacetyl-N'-(S)-t-butyl aspartyl ethylenediamine diamide

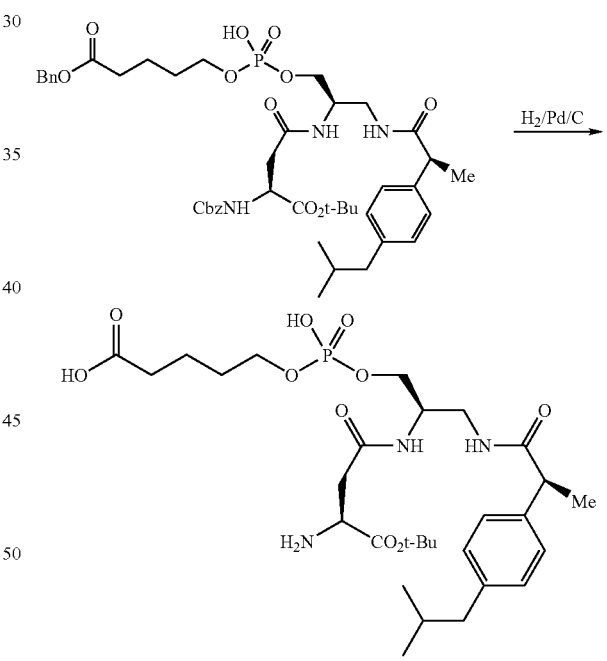

In a 500 mL Parr bottle, benzyl 5-oxy-pentanoate-phosphono-(R)-2-oxymethyl-N-(S)-4-Isobutyl-α-methylphenylacetyl-N'-(S)-N-benzyloxycarbonyl t-butyl aspartyl ethylenediamine diamide (0.289 g, 0.303 mmol) was dissolved in 15 mL anhydrous THF and the solution was degassed. 10% Palladium on carbon (0.200 g) was added under argon. The mixture was shaken for 14 h under 45 psi $H_2$. The catalyst was filtered off and rinsed several times with THF. Evaporation of solvent gave the desired amino acid as a white solid. Yield 0.193 g (87%). MS: 630.55 (M+1) and 1260.15 (2M+1).

Step 11: 5-Oxy-pentanoic acid-phosphono-(R)-2-oxymethyl-N-(S)-4-isobutyl-α-methylphenylacetyl-N'-(S)-t-butyl N-(3-methoxy-2,4,6-triiodobenzamide) aspartate ethylenediamine diamide

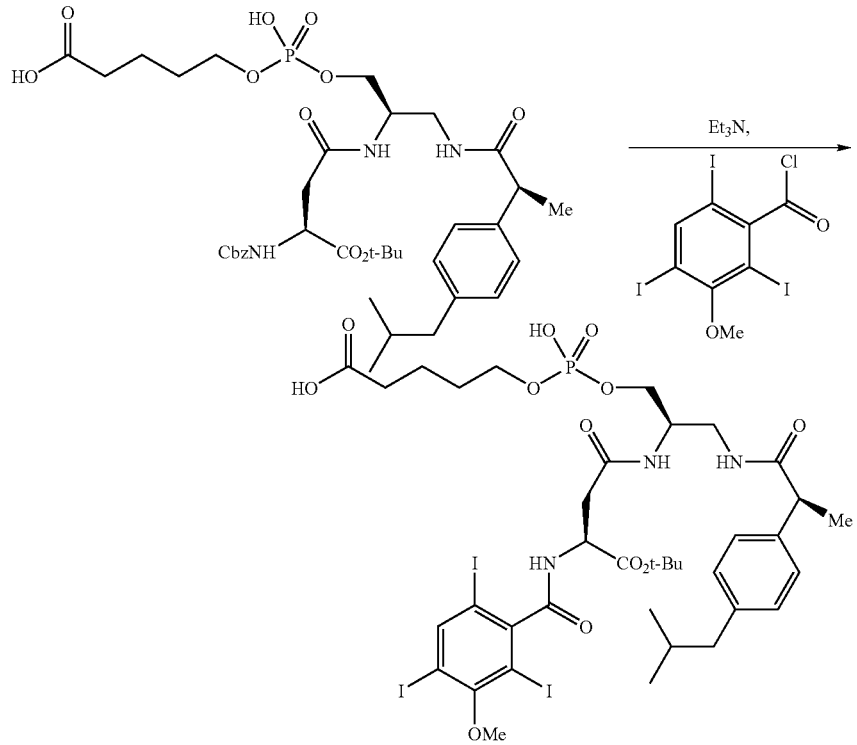

In a 25 mL pear shape flask, amine (0.075 g) methyl 3-methoxy-2,4,6-triiodobenzoyl chloride (0.062 g) was suspended in 1 mL anhydrous methylene chloride. Triethylamine (43 μL) was added at RT and the reaction mixture became homogeneous. The reaction mixture was stirred for 6 h at RT. The organic solvents and the aqueous layers were evaporated to dryness to give the crude desired amide which was used without any further purification in the next step. Yield 0.157 g (~100% crude). MS: 1142.55 (M+1).

Step 12: (N-Hydroxysuccinimide ester of 5-oxy-pentanoic acid)-phosphono-(R)-2-oxymethyl-N-(S)-4-isobutyl-α-methylphenylacetyl-N'-(S)-t-butyl N-(3-methoxy-2,4,6-triiodobenzamide)aspartate ethylenediamine diamide

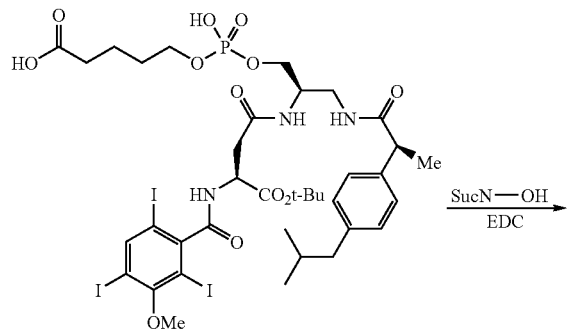

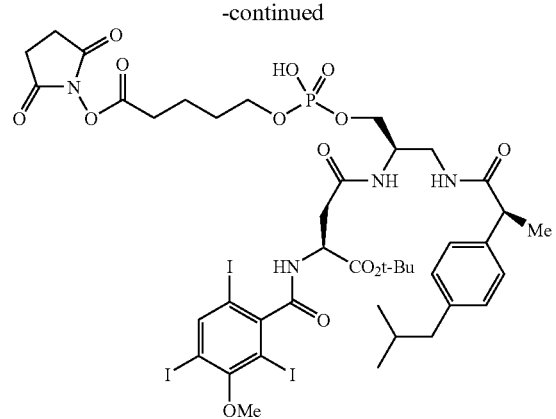

Acid (0.157 g) and N-hydroxysuccinimide (17.8 mg) were dissolved in 1 mL anhydrous methylene chloride. EDC (24.7 mg) was added at once at RT. Additional EDC (24.7 mg) and N-hydroxysuccinimide (17.8 mg) were added. After 16 h, methylene chloride was evaporated by rotary evaporation and the residue was dissolved in ethyl acetate. The ethyl acetate layer was washed with $H_2O$ and dried over $MgSO_4$. Evaporation of solvent gave the crude desired activated ester, which was purified by extracting the impurities with anhydrous ether. Yield 0.096 g (73%). MS: 1239.75 (M+1).

Step 13: (N-Hydroxysuccinimide ester of 5-oxy-pentanoic acid)-phosphono-(R)-2-oxymethyl-N-(S)-4-isobutyl-α-methylphenylacetyl-N'-(S)-N-(3-methoxy-2,4,6-triiodobenzamide) aspartate ethylenediamine diamide

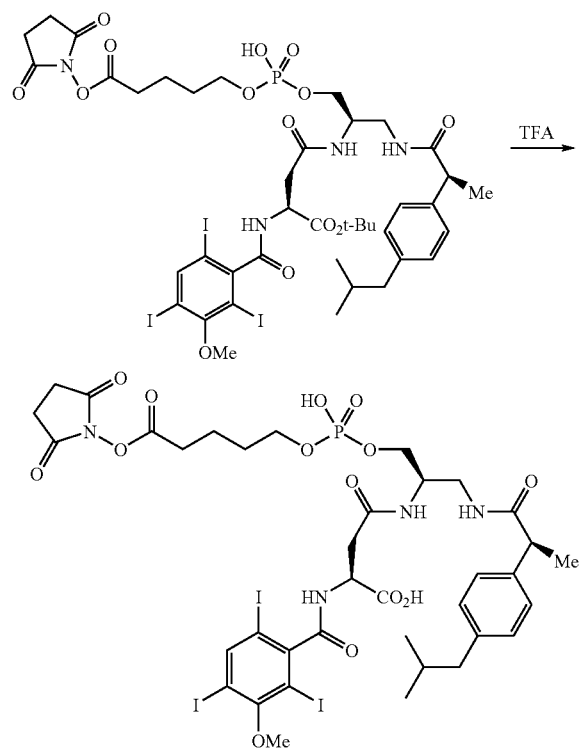

t-Butyl ester (0.050 g) was dissolved in 0.5 mL anhydrous methylene chloride. Trifluoroacetic acid (0.2 mL) was added at 0° C. and the reaction was stirred for 6 h at 0° C. The solvents were evaporated and the residue was washed with ether to give the desired acid as a white solid. Yield 0.033 g (72%). MS: 1183.55 (M+1).

Example 2

Synthesis and Characterization of Albumin Binding Reagents

5-oxy-pentanoic acid-phosphono-(R)-2-oxymethyl-N-(S)-4-isobutyl-α-methylphenylacetyl-N'-(S)-N-(3-methoxy-2,4,6-triiodobenzamide)aspartate ethylenediamine diamide Activated ester of 5-oxy-pentanoic acid-phosphono-(R)-2-oxymethyl-N-(S)-4-isobutyl-α-methylphenylacetyl-N'-(S)-N-(3-methoxy-2,4,6-triiodobenzamide)aspartate ethylenediamine diamide (5 mg) was dissolved in 1 mL saturated NaHCO₃. The reaction mixture was stirred for 1.5 h and then the diacid was precipitated by addition of 6N HCl. The solid was filtered and was purified by reverse phase preparative HPLC (C18, Acetonitrile/1% TFA). Yield 1 mg (20%, 94.3% pure by HPLC).

Step 1: Benzyl 7-aminoheptanoate p-toluenesulfonic salt

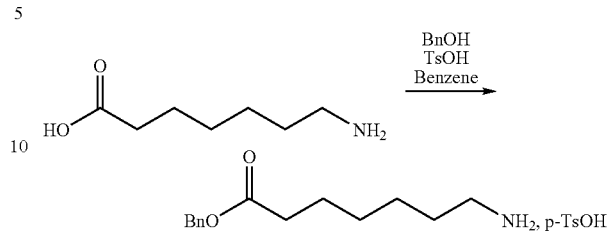

In a 100 mL 3-neck round-bottom flask equipped with a Dean Stark trap fitted with a condenser and filled with 4 Å molecular sieves, 7-aminoheptanoic acid (1.45 g) and p-TsOH, 1H₂O (2.00 g) were suspended in 40 ml benzene. Benzyl alcohol (5.2 ml) was added and the reaction mixture was refluxed for 20 h. The solvent was removed by rotary evaporation and the residue was triturated with ether to remove the excess benzyl alcohol. The desired product was obtained by filtration as a white solid. Yield 4.05 g (97%).

Step 2: (R)-2-N-tert-Butoxycarbonyl-3-N-(S)-4-isobutyl-α-methylphenylacetamide-2,3-diaminopropionic acid

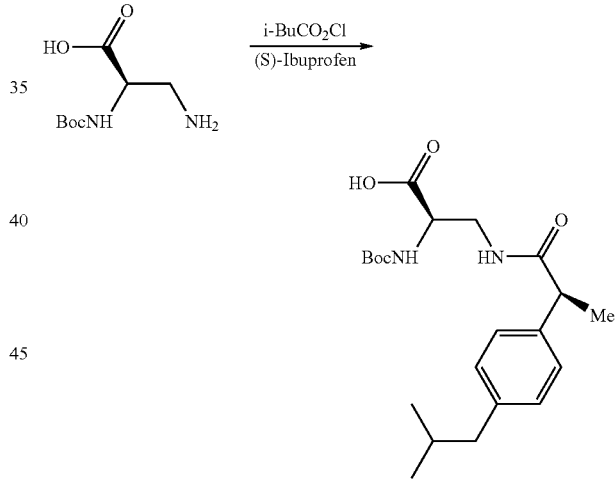

(S)-Ibuprofen (1.06 g) and triethylamine (0.7 mL) were dissolved in THF and the solution was cooled to −15° C. Isobutylchloroformate (0.67 mL) was added drop-wise and the white suspension was stirred for 20 minutes. A second equivalent of triethyl amine and the N-α-Boc diamino propionic acid (1.05 g) was added and the reaction was stirred overnight between 0° C. and RT. THF was evaporated under reduced pressure and residue was partitioned between saturated NaHCO₃ and ethyl acetate. The aqueous layer was extracted with ethyl acetate three times. The aqueous layer was acidified with 0.5 N KHSO₄ (pH=3) and was extracted again with ethyl acetate three times. The organic layers were combined and dried over Na₂SO₄. Evaporation of solvent gave the crude desired amide which was purified by flash chromatography on silica gel (CH₂Cl₂/MeOH). Yield 1.311 g (65%). MS: 293.45 (M+1-BOC), 415.45 (M+Na).

Step 3: Benzyl 7-amino heptanoate (R)-2-N-tert-butoxycarbonyl-3-N-(S)-4-isobutyl-α-methylphenylacetamide-2,3-diaminopropionamide Step 4: Benzyl 7-amino heptanoate (R)-2-N-(tert-butyl N-benzyloxycarbonyl aspartoyl)-3-N-(S)-4-isobutyl-α-methylphenylacetamide-2,3-diaminopropionamide

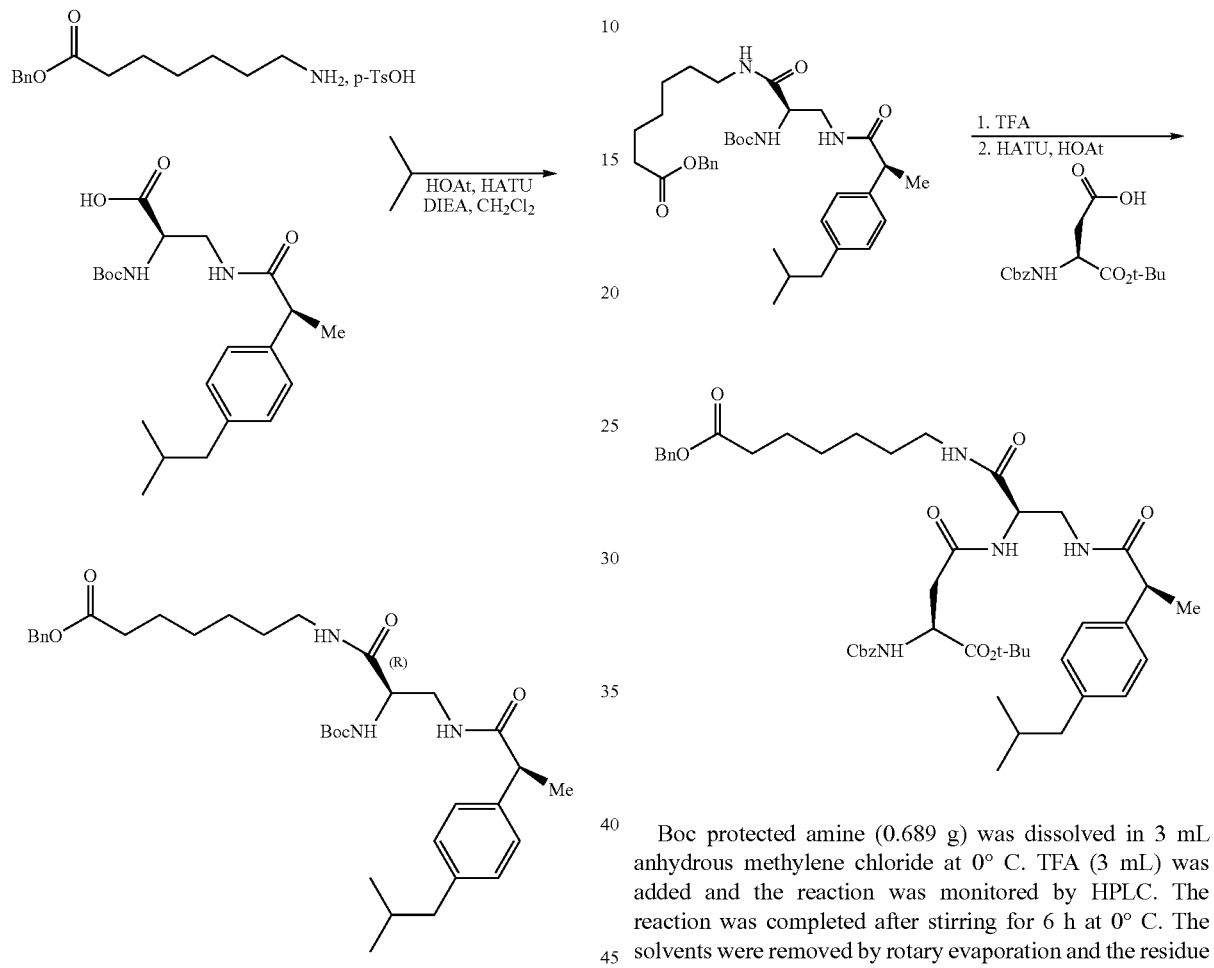

Acid (0.66 g) and HOAt (0.25 g) were dissolved in 5 mL anhydrous methylene chloride, and diisopropylethylamine (2.3 mL) and benzyl 7-aminoheptanoate p-toluenesulfonate salt (0.75 g) were added at 0° C. HATU (0.70 g) was added and the reaction mixture was stirred for 20 h between 0° C. and RT. Excess amine and un-reacted acid were scavenged with ultra-pure silicagel resins, isocyanate 1.54 mmol/g (1.0 g), and diamine 1.44 mmol/g (0.38 g) with stirring for 30 minutes at RT. The resins were filtered and the solvent was evaporated. The residue was partitioned between ethyl acetate and 0.5 N $KHSO_4$. The organic layer was washed with $KHSO_4$, saturated $NaHCO_3$ and brine. The organic layer was dried over $Na_2SO_4$. Evaporation of solvent gave the crude desired bis-amide which was purified by flash chromatography on silica gel (ethyl acetate/hexanes). Yield 0.030 g of (S) enantiomer (3%) and 0.729 g of (R) enantiomer (71%). MS: 510.55 (M+1-BOC), 610 (M+1), 632.75 (M+Na).

Boc protected amine (0.689 g) was dissolved in 3 mL anhydrous methylene chloride at 0° C. TFA (3 mL) was added and the reaction was monitored by HPLC. The reaction was completed after stirring for 6 h at 0° C. The solvents were removed by rotary evaporation and the residue was triturated 3 times with 3 mL 4M HCl in dioxane and the dioxane was evaporated. The white solid was triturated with ether, was filtered and dried under vacuum. The hydrochloride salt was used in the next step without any further purification. Yield 0.504 g (82%). MS: 510.55 (M+1).

Amine hydrochloride salt (0.504 g) was dissolved in 5 mL anhydrous methylene chloride and diisopropylethylamine (1.29 mL). tert-Butyl N-benzyloxyearbonyl aspartate dicyclohexyl ammonium salt (0.514 g), HATU (0.388 g) and HOAt, 1 $H_2O$ (0.139 g) were added at 0° C. and stirred 13.5 h between 0° C. and RT. Ultra-pure silica gel resins, isocyanate 1.54 mmol/g (1.0 g) and diamine 1.44 mmol/g (0.38 g) after stirring for 20 minutes at RT. The resins were filtered and the solvent was evaporated. The residue was partitioned between ethyl acetate and $H_2O$. The organic layer was washed 3 times with $H_2O$ and brine. The organic layer was dried over $MgSO_4$. Evaporation of solvent gave the crude desired product which was purified by flash chromatography on silica gel ($CH_2Cl_2$ to $CH_2Cl_2$/MeOH). Yield 0.663 g (88%). MS: 815.95 (M+1), 837.75 (M+Na).

Step 5: 7-Amino heptanoic acid (R)-2-N-(tert-butyl amino aspartoyl)-3-N-(S)-4-isobutyl-α-methylphenylacetamide-2,3-diaminopropionamide

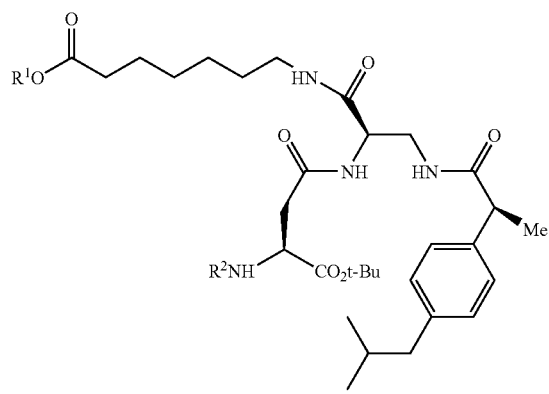

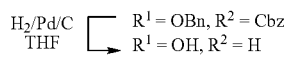

In a 500 mL Parr bottle, protected amino acid (0.653 g) was dissolved in THF and the solution was degassed. 10% Palladium on carbon (0.500 g) was added under argon. The mixture was shaken for 18 h under 45 psi $H_2$. Additional palladium catalyst (0.3 g) was added and the mixture was shaken under 45 psi $H_2$ for 18 hours. The catalyst was filtered off and rinsed several times with MeOH. Evaporation of solvent gave the desired amino acid as a white solid. Yield 0.490 g (~100% crude 95% pure by HPLC). MS: 591.55 (M+1) and 613.55 (M+Na).

Step 6: N-Hydroxysuccinimide ester of 7-amino heptanoic acid (R)-2-N-(N-(3-methoxy-2,4,6-triiodobenzamide)aspartoic acid-oyl)-3-N-(S)-4-isobutyl-α-methylphenylacetamide-2,3-diaminopropionamide

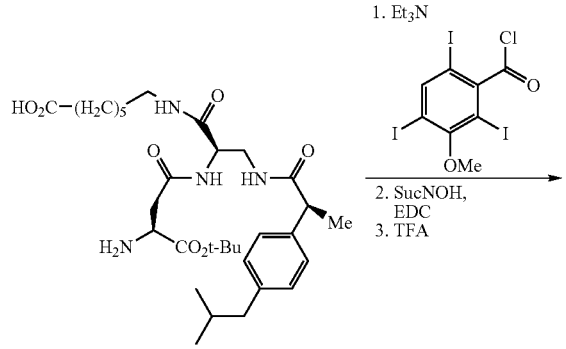

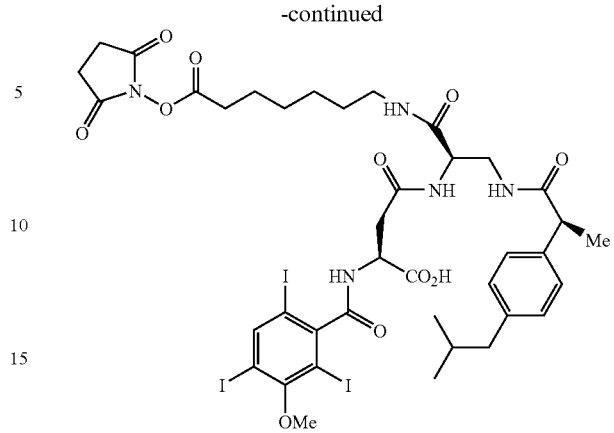

Amine-acid (0.300 g) was suspended in 2 mL anhydrous methylene chloride. Triethylamine (0.14 mL) was added and the mixture was stirred until most had dissolved. The solution was cooled to 0° C. 3-Methoxy-2,4,6-triiodobenzoyl chloride (0.274 g) dissolved in 0.5 mL anhydrous methylene chloride was added drop-wise. The reaction was stirred for 22 h. Solvent was evaporated and the resulting yellow foaming solid was triturated 4 times with ether and dry to give 0.60 g of a pale white solid which was purified by 2 flash chromatographies on silica gel ($CH_2Cl_2$/MeOH). Yield 0.221 g (50%). MS: 1103 (M+1).

Acid (0.117 g) was suspended in 4 mL anhydrous methylene chloride. N-Hydroxy succinimide (0.018 g) EDC (0.025 g) were added and the reaction was stirred for 26 h at RT. The reaction mixture was diluted with more methylene chloride, washed with $H_2O$, and dried over $MgSO_4$. The solvent was evaporated to give the desired activated ester as a yellowish solid. Yield 0.101 g (79%). MS: 1200.15 (M+1).

t-Butyl ester (0.050 g) was dissolved in a mixture of 1 mL anhydrous methylene chloride and 0.4 mL trifluoroacetic acid at 0° C. The reaction mixture was stirred between 0° C. and RT for 23 h. The solvents were evaporated. The residue was dried under vacuum for 24 h. Yield 46.2 mg (97%, 70% purity by HPLC). MS1144.15 (M+1) and 1166.15 (M+Na).

Step 7: 7-amino heptanoic acid (R)-2-N-(N-(3-methoxy-2,4,6-triiodobenzamide)aspartoyl))-3-N-(S)-4-isobutyl-α-methylphenylacetamide-2,3-diaminopropionamide

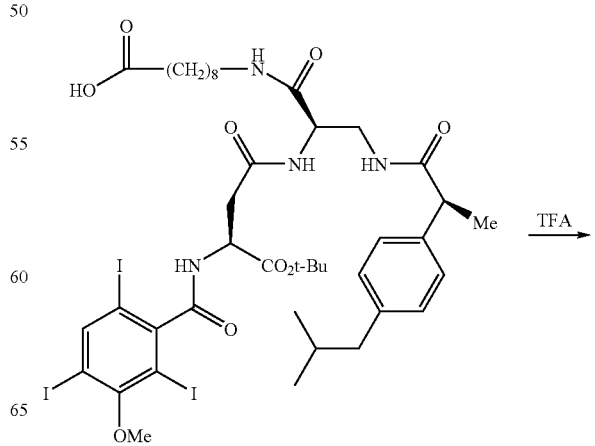

-continued

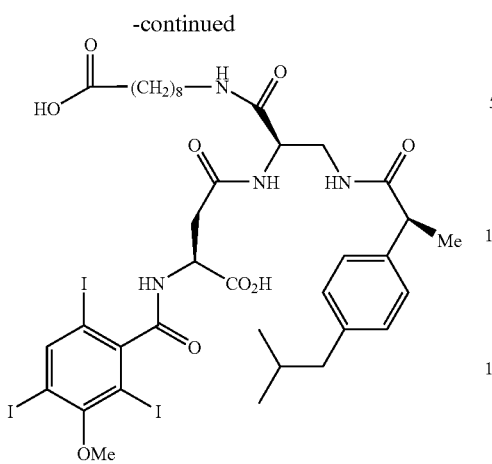

7-amino heptanoic acid (R)-2-N-(t-butyl N-(3-methoxy-2,4,6-triiodobenzamide) aspartoyl))-3-N-(S)-4-isobutyl-α-methylphenylacetamide-2,3-diaminopropionamide [an intermediate in the synthesis of N-Hydroxysuccinimide ester of 7-amino heptanoic acid (R)-2-N-(N-(3-methoxy-2,4,6-triiodobenzamide)aspartoic acid-oyl)-3-N-(S)-4-isobutyl-α-methylphenylacetamide-2,3-diaminopropionamide, above] (13 mg) was dissolved in 2 mL trifluoroacetic acid. The reaction was stirred for 3 h at 0° C. TFA was evaporated and the crude diacid was purified by reverse phase preparative HPLC (C18, Acetonitrile/1% TFA). Yield 3 mg (25%, 99% pure by HPLC).

Example 3

The affinities of a series of binding groups were obtained using a dansylsarcosine fluorescent probe, which strongly fluoresces when bound to HSA. The data shown in Table 1 below were determined as derivatives of a highly water soluble gadolinium chelate, Gd-DTPA, so that a relative rank order of binding group affinity could be obtained. Upon adding the binding group linked to the solubilizing fragment, a decrease in fluorescence indicated displacement by the albumin binding group. The data were fit to obtain an inhibition equilibrium constant, $K_i$, which reflects the affinity of the binding group for a given probe's binding site.

TABLE 1

| Binding Group | $K_i$ (4.5% HSA) |
| --- | --- |
|  | 0.7 μM |
|  | 0.9 μM |

TABLE 1-continued
| Binding Group | Ki (4.5% HSA) |
|---|---|
| | 0.92 μM |
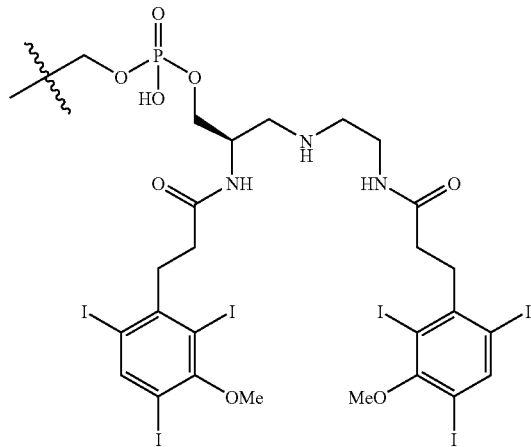
1.0 μM
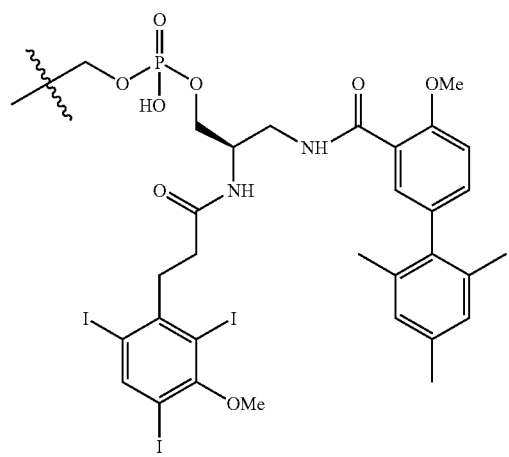
3.4 μM
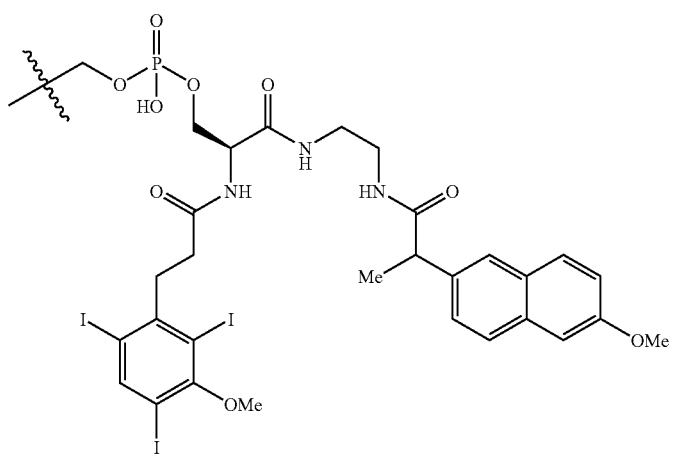

TABLE 1-continued
| Binding Group | Ki (4.5% HSA) |
| --- | --- |
| 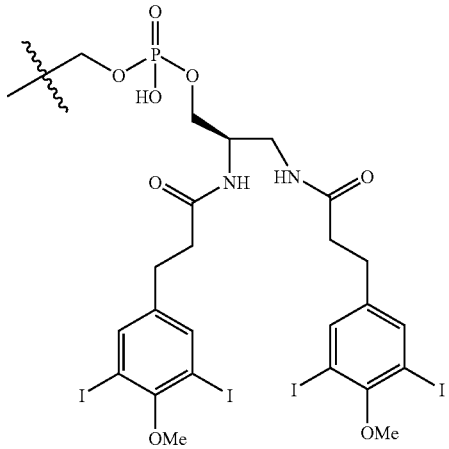 | 3.6 μM |
| 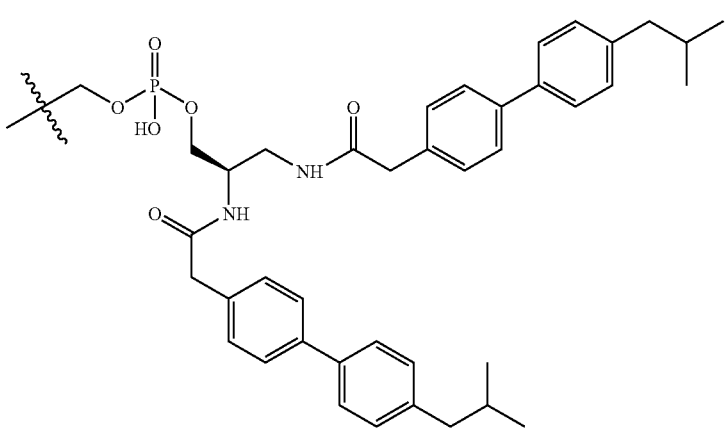 | 4.6 μM |
| 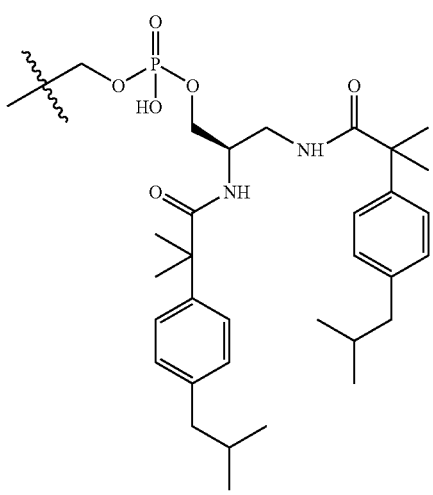 | 6.9 μM |

TABLE 1-continued

| Binding Group | Ki (4.5% HSA) |
|---|---|
| 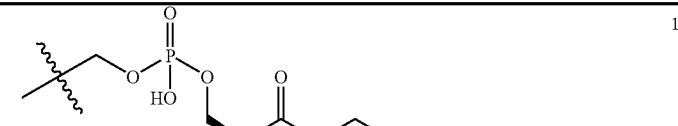 | 14.7 μM |

Example 4

Preparation of Insulin Conjugates 1–4

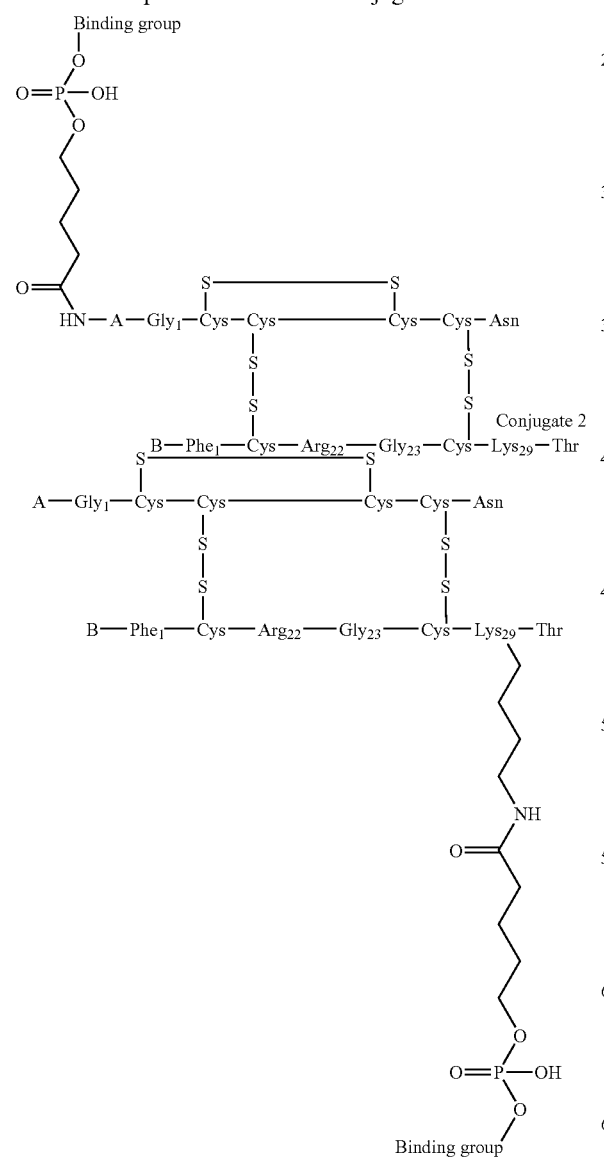

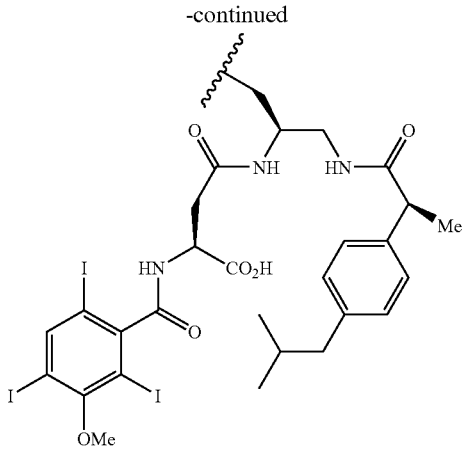

Recombinant human insulin (expressed in *E. Coli* (Sigma) (56 mg, 9.6 μmol., 2 eq.)), activated ester (1 eq.), and $Na_2CO_3$ (10 eq.) were suspended in 0.8 mL DMF at 0° C. Water (0.4 mL) was added and the mixture became almost homogeneous. The reaction mixture was stirred for 18 h between 0° C. and RT. The crude reaction mixture contained mostly a mixture of unreacted insulin and a 1:1 mixture of conjugate 2/conjugate 1. The mixture was separated by preparative HPLC (C-18, gradient: Acetonitrile/$NH_4OAc$ 50 mM 35% to 80%). Yield 28.3 mg insulin (50%), 11 mg conjugates 1 and 2 (33%). Batches of ≈2 mg of conjugate 1 and conjugate 2 were obtained after multiple preparative HPLC's.

Conjugate 1 MS: (z=3: 2293.8, z=4: 1720.6, z=5: 1376.6). A solution of conjugate 1 was treated with excess DTT and the mixture was incubated for 1 h at RT. An aliquot was analyzed by LC-MS and the following fragments were observed: Fragment 1: reduced B chain (z=2: 1715.75, z=3: 1144.15, z=4: 858.35), Fragment 2: reduced A chain acylated on Gly 1 (z=2: 1726.3, z=3: 1151.15).

Conjugate 2 MS: (z=3: 2293.8, z=4: 1720.8, z=5: 1375.9). A solution of conjugate 2 was treated with excess DTT and with a solution of trypsin. The mixture was incubated for 1 h at RT. An aliquot was analyzed by LC-MS and the following fragments were observed: Fragment 1: reduced A chain (z=2: 1193.0, z=3: 796.0), Fragment 2: Phe1-Arg22 fragment of reduced B chain (z=2: 1245.2, z=3: 830.5), Fragment 3: Gly23-Lys29-εNHCOR-Thr-30 fragment of reduced B chain (z=2: 2028.3, z=3: 1015.0), Fragment 4: acylated reduced chain PheI-Lys29-εNHCOR-Thr-30 (z=2: 2250.1, z=3: 1500.6), where R is an albumin binding group.

A competition assay specific for site-2 (ibuprofen site) binding (vs. dansylsarcosine as a probe) was performed to assess the affinity of conjugates. Conjugate-1 and conjugate-2 were tested, and had Ki values of 41 µM and 15 µM, respectively. Under physiological conditions, these conjugates would be >98% bound.

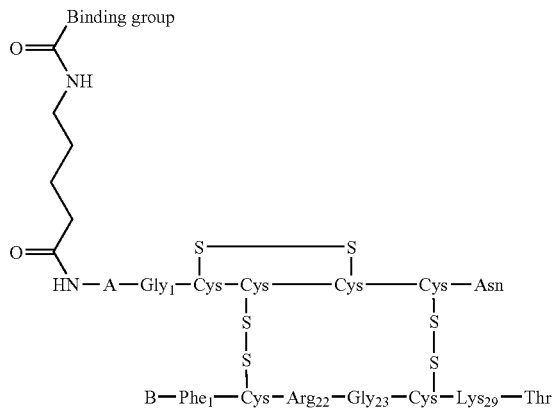

Conjugate 3

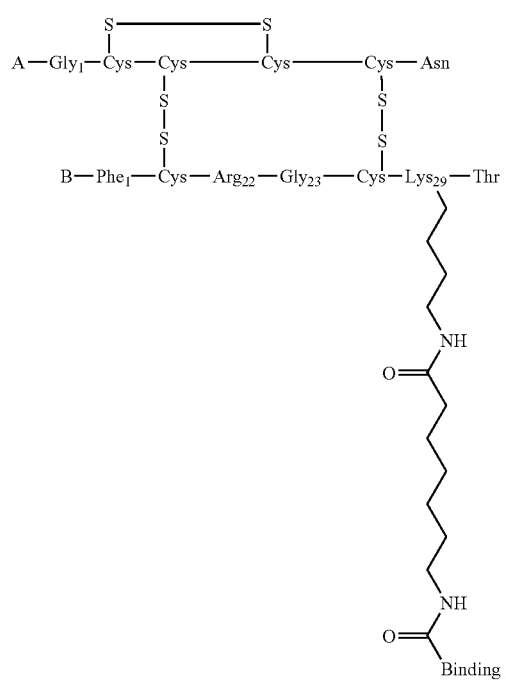

Conjugate 4

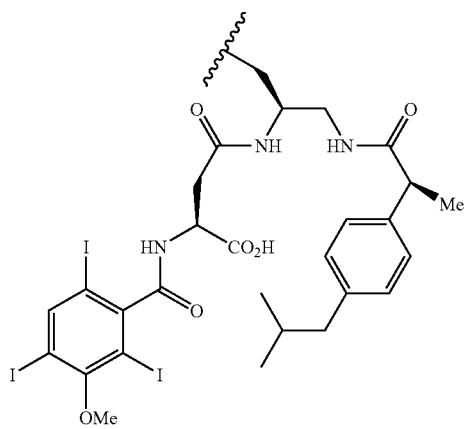

Binding group

Recombinant human insulin (expressed in *E. Coli* (Sigma) (152.4 mg, 26.2 µmol., 3 eq.)) was dissolved in 0.8 mL of 1:1 mixture of DMF and $H_2O$ and $Na_2CO_3$ (3 eq.) was added at once. Activated ester (1 eq.) was added portionwise over 5 minutes. The reaction was complete after 6 h. The crude reaction mixture contained mostly a mixture of un-reacted insulin and a 2.6:1 mixture of conjugate 4/conjugate 3. The mixture was separated by preparative HPLC (C-18, gradient: Acetonitrile/$NH_4OAc$ 50 mM 35% to 80%). Yield 87 mg insulin (86%), 6.5 mg conjugate 3 (11%) and 18.2 mg conjugate 4 (30%).

Conjugate 3 MS: (z=2: 1709.8) A solution of conjugate 3 was treated with excess DTT and with a solution of trypsin. The mixture was incubated for 1 h at RT. An aliquot was analyzed by LC-MS and the following fragments were observed: Fragment 1: reduced B chain (z=4: 859.6), Fragment 2: fragment of B chain (z=2: 1244.8, z=3: 830.2), Fragment 3: A chain Gly1-COR (z=2: 1707.0), where R is an albumin binding group.

Conjugate 4 MS (z=3: 2278.7, z=4: 1709.6). A solution of conjugate 4 was treated with excess DTT and with a solution of trypsin. The mixture was incubated for 1 h at RT. An aliquot was analyzed by LC-MS and the following fragments were observed: Fragment 1: Phe1-Arg22 fragment of reduced B chain (z=2: 1245.0, z=3: 830.4), Fragment 2: reduced A chain (z=2: 1192.3), Fragment 3: Gly23-Lys29-εNHCOR-Thr-30 fragment of reduced B chain (z=1: 1990.6, z=2: 995.0), Fragment 4: acylated reduced chain Phe1-Lys29-εNHCOR-Thr-30 (z=2: 2229.8, z=3: 1487.0), where R is an albumin binding group.

Example 5

Pharmacokinetic Study

Insulin is a convenient model for demonstrating the effects of albumin-binding on pharmacokinetic and pharmacodynamic profiles because the assays for insulin activity are well developed, the polypeptide is relatively inexpensive, and methods for selectively chemically modifying individual amino acids are well known.

Conjugates-1 and -2 and native human insulin were iodinated at New England Nuclear by reaction with lactoperoxidase and Na$^{125}$I to yield radiolabeled derivatives (roughly 0.01 mole Iodine/mole insulin) suitable for conducting pharmacokinetic studies in rabbits. The $^{125}$I-labeled samples were analyzed by HPLC on a C18 column, and three peaks of radioactivity were observed in each sample: a peak corresponding to insulin (or conjugate) at t=8–10 min (75–90% of the total $^{125}$I) and peaks of unknown origin at t=3 min and t=16 min. In calculating the specific activity of the insulin (μCi/μg), the amount of insulin in each sample was measured before iodination by amino acid analysis, and a 90% yield factor was applied to compensate for loss resulting from the iodination procedure. The specific activity of the insulin in the injected solution was further corrected for the presence of $^{125}$I-containing impurities. This final value was used to calculate the concentration of insulin (or conjugates) in plasma (μg/L) from the measured cpm values.

Anaesthetized white New Zealand rabbits (n=1 per compound) were injected with 100 μg of either [$^{125}$I]-insulin, or [$^{125}$I]-conjugate-1 or -2, a dose equivalent to ~0.8 U/kg. Blood samples (1 mL) were obtained at t=1, 3, 5, 7, 10, 15, 20, 25, 30, 45, 60, 75, 90, 120, 150, 180, 210, 240 and 270 min. Samples were centrifuged (1500 g, 10 min) to isolate the plasma fraction within 15 min of blood collection and frozen. Aliquots of plasma were counted as an initial estimate of the total compound in the blood.

HPLC Analysis: In order to determine the percentage of radioactivity arising from insulin or the conjugates and other products, the plasma samples were treated with 50% MeOH to precipitate albumin and other proteins. The supernatant was chromatographed on a C18 column (20 min gradient, 5–95% ACN) and fractions (1 min) were collected and counted (Packard μ-counter) to determine the radioactivity in each peak. To determine the counts in plasma due to insulin, the percentage in the insulin peak of the total $^{125}$I was multiplied by the total counts in the plasma.

The total cpm in plasma was multiplied in the sample by the percentage of activity in the insulin peak (or conjugate), as determined by HPLC analysis, and converted to μg/L. Plots of the total $^{125}$I plasma activity (without HPLC speciation) were compared to the plasma levels of insulin (or conjugate) species, calculated using the factors determined from HPLC analysis. For the insulin data, the baseline of the actual $^{125}$I activity assigned to insulin tails toward zero, whereas the total plasma $^{125}$I data levels out at a value equal to ~20% of the initial plasma concentration (see FIG. 1). A substantial overestimation of the AUC and half-life PK parameters would occur in the absence of the HPLC speciation that differentiates $^{125}$I-labeled insulin from $^{125}$I-labeled metabolites. The total plasma cpm data and the HPLC speciation data for the conjugates, on the other hand, parallel each other closely since the level of these compounds as a fraction of the total $^{125}$I remains fairly constant over the time course. Conjugates-1 and -2 were considerably longer lived in plasma than insulin. These decrease to only half their initial level after ~4–5 hr., whereas insulin is rapidly removed from the plasma and is barely detectable after 1 hr. The biological half-life of soluble monocomponent insulin in rabbits following subcutaneous injection is reported to be 5.50±0.49 minutes. [T. Kasama et al., J. Pharm. Dyn. 3, 206–212 (1980)].

Data ([insulin] vs. time) were fit to a two compartment, bolus injection pharmacokinetic model. All data sets fit well to this model. Parameters were calculated using the computer program "PharSite", fitting to a two compartment/bolus injection model ($C_t = Ae^{-\alpha t} + Be^{-\beta t}$, Ct=concentration of species of interest at time=t; A, B, α, and β are fit parameters). Data were normalized to dose. Uncertainty in the parameters ranges from 10–20%. Residual plots from the fits gave approximately random distributions, further indicating that the chosen model was appropriate. The values of the parameters obtained from the fits are displayed in Table 2.

TABLE 2

Rabbit PK Data

| Parameter** | Insulin | Conjugate-1 | Conjugate-2 |
|---|---|---|---|
| α Half-Life (min) | 4.2 | 5.1 | 44 |
| β Half-Life (min) | 100 | 160 | 520 |
| A (μg/L) | 220 | 210 | 330 |
| B (μg/L) | 30 | 1040 | 660 |
| Cmax (μg/L) | 250 | 1250 | 990 |
| CL (μL/min/kg) | 5.9 | 0.12 | 0.053 |
| Vss (L/kg) | 0.62 | 0.026 | 0.039 |
| AUC (min*μg/L) | 5340 | 236000 | 517000 |
| AUC Fold Increase | 1 | 44 | 97 |

The plasma PK plots for insulin and the conjugates are biphasic with an initial sharp decrease in drug concentration followed by a shallow slope of long duration. For insulin, this initial decrease is considerably more acute than for the conjugates, accounting for the large difference in AUC. The concentration of the conjugates remains high throughout the time course, resulting in AUC values for conjugate-1 and conjugate-2 that are 44-fold and 97-fold higher than that measured for insulin. The volume of distribution (Vss) value for insulin is 0.6 L/kg, suggesting considerable organ uptake, while the values for the conjugates are close to 0.03–0.04 L/kg, consistent with localization to the plasma compartment. The lower clearance rate (CL) and higher Cmax (maximal plasma concentration) for the conjugates than for insulin also reflect the improved plasma stability conferred to insulin by conjugation with an albumin-binding group.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:
1. A compound having the formula:

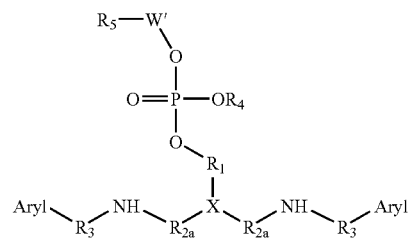

wherein $R_1$ is $(CH_2)_n$, where n is an integer from 0 to 12; $R_{2a}$ and $R_{2b}$ are independently $(CH_2)_m$, $C(O)NH-(CH_2)_x$, $CH_2-NH-(CH_2)_y$, $(CH_2)_z-C(O)$, or not present, where m, x, and z are integers from 0 to 12 and y is an integer from 1 to 12;

$R_3$ is independently $C(O)—(CH_2)_p$, where p is an integer of 0 to 12, $C(O)CH(CH_3)$, $C(O)C(CH_3)_2$, or is not present;

$R_4$ is H, alkyl, or a negative charge and the salts thereof;

X is N, CH, P, or triazine;

W' is a linear or branched alkyl chain having one or more carbon atoms; and $R_5$ is halogen, 1° amine, 2° amine, 3° amine, hydroxyl, thiol, carboxylic acid, sulfonic acid, or activated ester.

2. A compound having the formula:

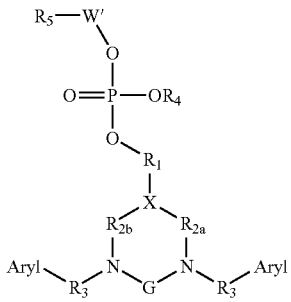

wherein $R_1$ is $(CH_2)_n$, where n is an integer from 0 to 12;

$R_{2a}$ and $R_2$ are independently $(CH_2)_m$, $C(O)NH—(CH_2)_x$, $CH_2—NH—(CH_2)_y$, $(CH_2)_z—C(O)$, or not present, where m, x, and z are integers from 0 to 12 and y is an integer from 1 to 12.

$R_3$ is independently $C(O)—(CH_2)_p$, where p is an integer of 0 to 12, $C(O)CH(CH_3)$, $C(O)C(CH_3)_2$, or is not present.

$R_4$ is H, alkyl, or a negative charge and the salts thereof;

X is N, CH, P, or triazine;

W' is a linear or branched alkyl chain having one or more carbon atoms; and $R_5$ is halogen, 1° amine, 2° amine, 3° amine, hydroxyl, thiol, carboxylic acid, sulfonic acid, or activated ester; and G is $(CH_2)_q$, where q is an integer from 0 to 9, C(O), $SO_2$, or S(O).

3. The compound of claims 1 or 2, wherein one or more of said carbon atoms of W' are substituted independently with cycloalkane, a heteroatom, a substituted heteroatom, CO—O, CO—NH, CO—S, CO, $SO_2$, $SO_2$—NH, or $SO_2$—O.

4. The compound of claim 3, wherein the substituted heteroatom is selected from the group consisting of N-(alkyl), N-(aryl), N-(alkyl-aryl), phosphine, phosphate, thiophosphate, phosphodiester, and aminophosphate.

5. The compound according to claim 1 or 2, wherein the aryl moieties are independently

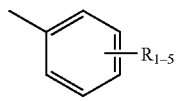

wherein R is selected from the group consisting of H, $OCH_3$, halogen, CN, $NO_2$, $CF_3$, $OCF3$, OH, $O(C_1-C_4)Alkyl$, SH, $S(C_1-C_4)Alkyl$, $SO(C_1-C_4)Alkyl$, $SO_2(C_1-C_4)Alkyl$, $SO3H$, $SO_2NH_2$, $SO_2NH(C_1-C_4)Alkyl$, $NH_2$, $NH(C_1-C_4)Alkyl$, $N((C_1-C_4)Alkyl)_2$, $CO_2H$, $(C_1-C_6)Alkyl$, and $(C_3-C_8)Cycloalkyl$.

6. The compound according to claim 5, wherein the aryl moiety is selected from the group consisting of:

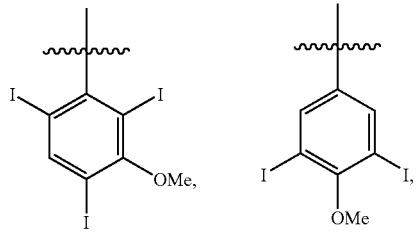

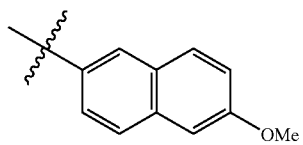

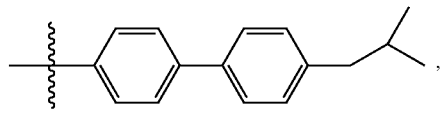

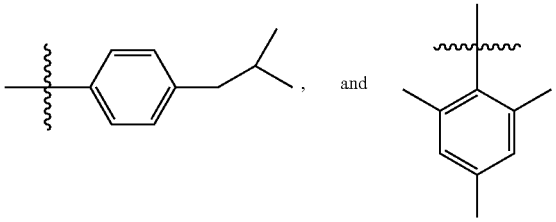

7. A conjugated polypeptide having the general Formula I,

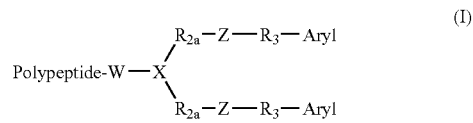

wherein $R_{2a}$ and $R_{2b}$ are independently $(CH_2)_m$, $C(O)NH—(CH_2)_x$, $CH_2—NH—(CH_2)_y$, $(CH_2)_z—C(O)$, or not present, where m, x, and z are integers from 0 to 12 and y is an integer from 1 to 12;

$R_3$ is independently $C(O)—(CH_2)_p$, where p is an integer of 0 to 12, $C(O)CH(CH_3)$, $C(O)C(CH_3)_2$, or is not present;

X is N, CH, P, or triazine;

W is a linear or branched alkyl chain having one or more carbon atoms;

Z is independently NH, O, S, S(O), $CH_2$, NH—CO, $SO_2$, CH—R, $C(R)_2$, CH=CH, CH=N, wherein R is alkyl or aryl; and wherein the conjugated polypeptide specifically binds to albumin.

8. A conjugated polypeptide having the general Formula II:

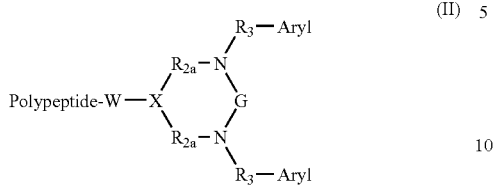

wherein $R_{2a}$, $R_{2b}$, and $R_3$ independently comprise a linear chain of 0 to 14 atoms;
X is one atom or 5 or more atoms, wherein the 5 or more atoms form a cyclic or a heterocyclic ring structure;
W is a linker; and
G is a chain of 0 to 9 carbon atoms,
wherein the conjugated polypeptide specifically binds to albumin.

9. The conjugated polypeptide of claim 8, wherein $R_{2a}$ and $R_{2b}$ are independently $(CH_2)_m$, $C(O)NH-(CH_2)_x$, $CH_2-NH-(CH_2)_y$, $(CH_2)_z-C(O)$, or not present, where m, x, and z are integers from 0 to 12 and y is an integer from 1 to 12.

10. The conjugated polypeptide of claim 8 or 9, wherein $R_3$ is independently $C(O)-(CH_2)_p$, where p is an integer of 0 to 12, $C(O)CH(CH_3)$, $C(O)C(CH_3)_2$, or is not present.

11. The conjugated polypeptide of any one of claims 8 or 9, wherein X is N, CH, P, or triazine.

12. The conjugated polypeptide of any one of claims 8 or 9, wherein G is $(CH_2)_q$, where q is an integer from 0 to 9, or C(O).

13. The conjugated polypeptide of claims 7 or 8, wherein the conjugate comprises a therapeutic polypeptide selected from the group consisting of erythropoietin, insulin, interferon α-2b, interferon β, interferon γ, granulocyte colony stimulating factor, human growth hormone, granulocyte macrophage colony stimulating factor, relaxin, urokinase, streptokinase, tissue plasminogen activator, and tumor necrosis factor.

14. The conjugated polypeptide according to claims 7 or 8, wherein the conjugate specifically binds to site II of albumin.

15. The conjugated polypeptide according to claims 7 or 8, wherein the conjugate exhibits a serum half-life that is greater than that of the corresponding unconjugated polypeptide.

16. The conjugated polypeptide of claim 8, wherein W comprises a structural element having the formula,

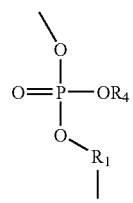

wherein $R_1$ is $(CH_2)_n$, where n is an integer from 0 to 12; and
$R_4$ is H, alkyl, or a negative charge and the salts thereof.

17. The conjugated polypeptide of claim 8, wherein W comprises a structural element having the formula,

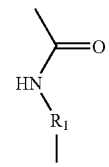

wherein $R_1$ is $(CH_2)_n$, and where n is an integer from 0 to 12.

18. The conjugated polypeptide of claim 8, wherein W comprises a linear or branched alkyl chain having one or more carbon atoms.

19. The conjugated polypeptide of claims 7 or 18, wherein one or more of said carbon atoms of W are substituted independently with cycloalkane, a heteroatom, a substituted heteroatom, CO—O, CO—NH, CO—S, CO, $SO_2$, $SO_2$—NH, or $SO_2$—O.

20. The conjugated polypeptide of claim 19, wherein the substituted heteroatom is selected from the group consisting of N(alkyl), N(aryl), and N(alkyl-aryl), phosphine, phosphate, thiophosphate, phosphodiester, and aminophosphate.

21. The conjugated polypeptide of claims 7 or 8, wherein the aryl moieties are independently

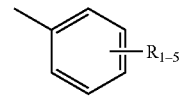

wherein R is selected from the group consisting of H, $OCH_3$, halogen, CN, $NO_2$, $CF_3$, $OCF_3$, OH, $O(C_1-C_4)alkyl$, SH, $S(C_1-C_4)alkyl$, $SO(C_1-C_4)alkyl$, $SO_2(C_1-C_4)alkyl$, $SO_3H$, $SO_2NH_2$, $SO_2NH(C_1-C_4)alkyl$, $NH_2$, $NH(C_1-C_4)alkyl$, $N((C_1-C_4)alkyl)_2$, $CO_2H$, $(C_1-C_6)alkyl$, and $(C_3-C_8)cycloalkyl$.

22. The conjugated polypeptide according to claim 21, wherein the aryl moiety is selected from the group consisting of:

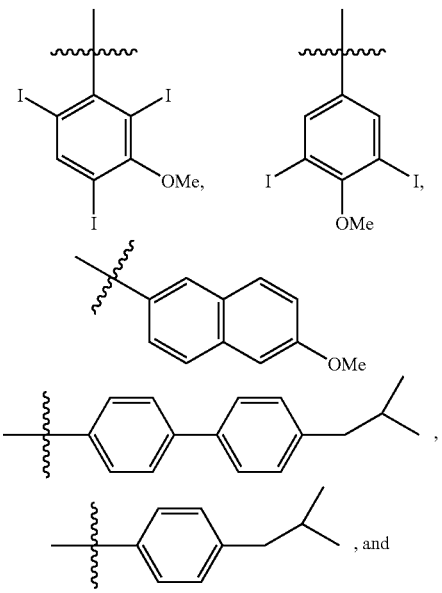

-continued

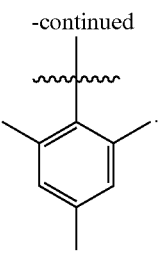

23. The compound according to claim 1, wherein the activated ester is selected from the group consisting of acid chloride, acid anhydride, maleimide, aldehyde, and N-hydroxysuccinimide (NHS) ester.

24. A conjugated polypeptide having the general Formula III:

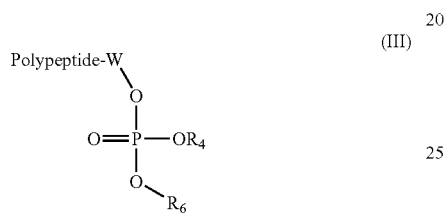

wherein $R_4$ is H, alkyl, or a negative charge and the salts thereof;

$R_6$ comprises a binding moiety containing one or more carbon atoms;

W is a linear or branched alkyl chain having one or more carbon atoms;

wherein the conjugated polypeptide binds albumin, and comprises a therapeutic polypeptide selected from the group consisting of erythropoietin, insulin, interferon α-2b, interferon β, interferon γ, granulocyte colony stimulating factor, human growth hormone, granulocyte macrophage colony stimulating factor, relaxin, urokinase, streptokinase, tissue plasminogen activator, and tumor necrosis factor.

25. The conjugated polypeptide of claim 24, wherein one or more of said carbon atoms of W are substituted independently with cycloalkane, a heteroatom, a substituted heteroatom, CO—O, CO—NH, CO—S, CO, $SO_2$, $SO_2$—NH, or $SO_2$—O.

26. The conjugated polypeptide of claim 25, wherein the substituted heteroatom is selected from the group consisting of N-(Alkyl), N-(Aryl), and N-(Alkyl-Aryl), phosphine, phosphate, thiophosphate, phosphodiester, and aminophosphate.

27. The conjugated polypeptide of claim 26, wherein $R_6$ further comprises at least one reactive moiety selected from the group consisting of halogen, 1° amine, 2° amine, 3° amine, hydroxyl, thiol, carboxylic acid, sulfonic acid, and activated ester.

28. The conjugated polypeptide of claim 27, wherein the activated ester is selected from the group consisting of acid chloride, acid anhydride, maleimide, aldehyde, and N-hydroxysuccinimide (NHS) ester.

29. The compound according to claim 1, wherein n is 1, $R_{2a}$ is $CH_2$—NH—$(CH_2)_2$, $R_{2b}$ is not present, $R_4$ is H; and X is CH.

30. The compound according to claim 29, wherein the aryl moiety is

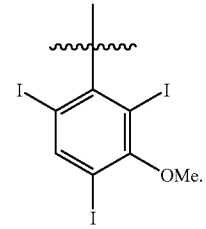

31. The compound according to claim 1, wherein n is 1, $R_{2a}$ is C(O)—NH—$(CH_2)_2$, $R_{2b}$ is not present, $R_4$ is H; and X is CH.

32. The compound according to claim 1, wherein the aryl moiety is selected from the group consisting of

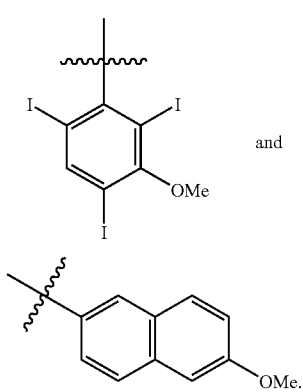

33. The compound according to claim 1, wherein n is 1, $R_{2a}$ is $CH_2$, $R_{2b}$ is not present, $R_4$ is H, and X is CH.

34. The compound according to claim 1, wherein the aryl moiety is selected from the group consisting of:

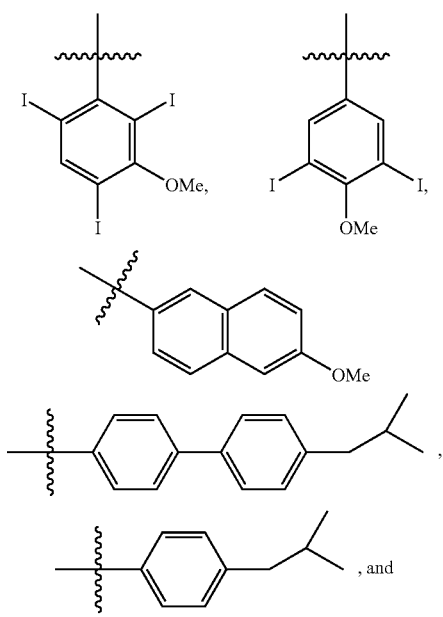

-continued

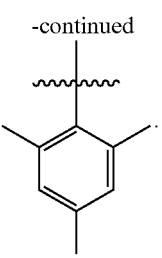

35. A method for increasing the half life of a polypeptide, the method comprising conjugating a therapeutic polypeptide to the compound of claim 1 or claim 2.

36. The compound of claim 2, wherein if said X is triazine, said triazine forms a bicyclic ring structure together with the ring defined by $R_{2a}$, $R_{2b}$, the two Ns, and the G.

37. The conjugated polypeptide of claim 8, wherein said cyclic or heterocyclic ring structure of X forms a bicyclic ring structure together with the ring defined by $R_{2a}$, $R_{2b}$, the two Ns, and the G.

38. A compound having the formula:

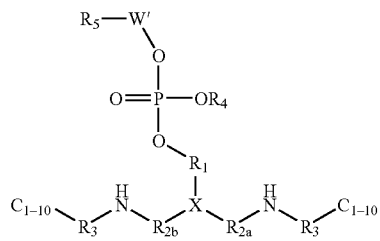

wherein $R_1$ is $(CH_2)_n$, where n is an integer from 0 to 12;
$R_{2a}$ and $R_{2b}$ are independently $(CH_2)_m$, $C(O)NH—(CH_2)_x$, $CH_2—NH—(CH_2)_y$, $(CH_2)_z—C(O)$, or not present, where m, x, and z are integers from 0 to 12 and y is an integer from to 12;
$R_3$ is independently $C(O)—(CH_2)_p$, where p is an integer of 0 to 12, $C(O)CH(CH_3)$, $C(O)C(CH_3)_2$, or is not present;
$R_4$ is H, alkyl, or a negative charge and the salts thereof;
X is N, CH, P, or triazine;
W' is a linear or branched alkyl chain having one or more carbon atoms;
$R_5$ is halogen, 1° amine, 2° amine, 3° amine, hydroxyl, thiol, carboxylic acid, sulfonic acid, or activated ester; and
$C_{1-10}$ comprises a non-aromatic moiety having 1–10 carbon atoms.

39. A compound having the formula:

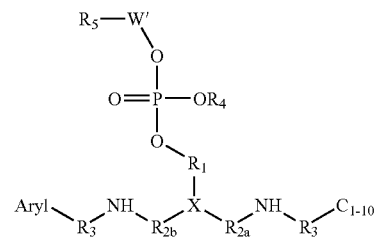

wherein $R_1$ is $(CH_2)_n$, where n is an integer from 0 to 12;
$R_{2a}$ and $R_{2b}$ are independently $(CH_2)_m$, $C(O)NH—(CH_2)_x$, $CH_2—NH—(CH_2)_y$, $(CH_2)_z—C(O)$, or not present, where m, x, and z are integers from 0 to 12 and y is an integer from 1 to 12;
$R_3$ is independently $C(O)—(CH_2)_p$, where p is an integer of 0 to 12, $C(O)CH(CH_3)$, $C(O)C(CH_3)_2$, or is not present;
$R_4$ is H, alkyl, or a negative charge and the salts thereof;
X is N, CH, P, or triazine;
W' is a linear or branched alkyl chain having one or more carbon atoms;
$R_5$ is halogen, 1° amine, 2° amine, 3° amine, hydroxyl, thiol, carboxylic acid, sulfonic acid, or activated ester; and
$C_{1-10}$ comprises a non-aromatic moiety having 1–10 carbon atoms.

40. A compound having the formula:

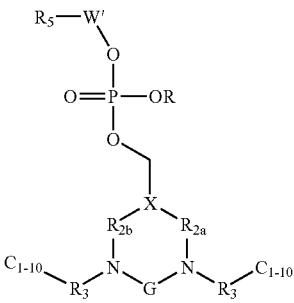

wherein $R_1$ is $(CH_2)_n$, where n is an integer from 0 to 12;
$R_{2a}$ and $R_{2b}$ are independently $(CH_2)_m$, $C(O)NH—(CH_2)_x$, $CH_2—NH—CH_2)_y$, $(CH_2)_z—C(O)$, or not present, where m, x, and z are integers from 0 to 12 and y is an integer from 1 to 12.
$R_3$ is independently $C(O)—(CH_2)_p$, where p is an integer of 0 to 12, $C(O)CH(CH_3)$, $C(O)C(CH_3)_2$, or is not present.
$R_4$ is H, alkyl, or a negative charge and the salts thereof;
X is N, CH, P, or triazine;
W' is a linear or branched alkyl chain having one or more carbon atoms;
$R_5$ is halogen, 1° amine, 2° amine, 3° amine, hydroxyl, thiol, carboxylic acid, sulfonic acid, or activated ester;
G is $(CH_2)_q$, where q is an integer from 0 to 9, $C(O)$, $SO_2$, or $S(O)$; and
$C_{1-10}$ comprises a non-aromatic moiety having 1–10 carbon atoms.

41. A compound having the formula:

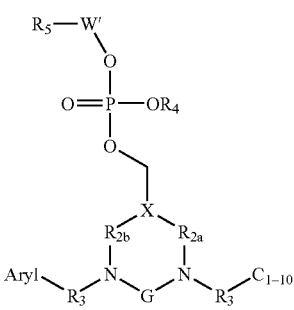

wherein $R_1$ is $(CH_2)_n$, where n is an integer from 0 to 12;

$R_{2a}$ and $R_{2b}$ are independently $(CH_2)_m$, $C(O)NH-(CH_2)_x$, $CH_2-NH-(CH_2)_y$, $(CH_2)_z-C(O)$, or not present, where m, x, and z are integers from 0 to 12 and y is an integer from 1 to 12.

$R_3$ is independently $C(O)-(CH_2)_p$, where p is an integer of 0 to 12, $C(O)CH(CH_3)$, $C(O)C(CH_3)_2$, or is not present.

$R_4$ is H, alkyl, or a negative charge and the salts thereof;

X is N, CH, P, or triazine;

W' is a linear or branched alkyl chain having one or more carbon atoms;

$R_5$ is halogen, 1° amine, 2° amine, 3° amine, hydroxyl, thiol, carboxylic acid, sulfonic acid, or activated ester;

G is $(CH_2)_q$, where q is an integer from 0 to 9, $C(O)$, $SO_2$, or $S(O)$; and $C_{1-10}$ comprises a non-aromatic moiety having 1–10 carbon atoms.

42. The compound of any one of claims 38, 39, 40, or 41, wherein the non-aromatic moiety comprises a linear, branched, or cyclic alkyl, alkenyl, or alkynyl moiety.

43. The compound of claim 42, wherein the cyclic moiety comprises one or more heteroatoms.

44. The compound of claim 43, wherein the heteroatom is selected from the group consisting of N, O, and S.

* * * * *